(12) United States Patent
Tam et al.

(10) Patent No.: US 6,458,069 B1
(45) Date of Patent: *Oct. 1, 2002

(54) MULTI LAYER RADIATION DELIVERY BALLOON

(75) Inventors: Lisa A. Tam, Lake Forest, CA (US); Brett A. Trauthen, Newport Beach, CA (US)

(73) Assignee: Endology, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/382,302

(22) Filed: Aug. 24, 1999

Related U.S. Application Data

(63) Continuation-in-part of application No. 09/253,433, filed on Feb. 19, 1999, now abandoned, and a continuation-in-part of application No. 09/256,337, filed on Feb. 19, 1999, now Pat. No. 6,287,249, which is a continuation-in-part of application No. 09/025,921, filed on Feb. 19, 1998, now abandoned, application No. 09/382,302, which is a continuation-in-part of application No. 09/040,172, filed on Mar. 17, 1998, now Pat. No. 6,149,574.

(51) Int. Cl.$^7$ ................................................ A61N 5/00
(52) U.S. Cl. ........................................................ 600/3
(58) Field of Search ........................................ 600/1–8

(56) References Cited

U.S. PATENT DOCUMENTS

| | | |
|---|---|---|
| 3,324,847 A | 6/1967 | Zoumboulis |
| 4,115,536 A | 9/1978 | Rothman et al. |
| 4,124,705 A | 11/1978 | Rothman et al. |
| 4,126,669 A | 11/1978 | Rothman et al. |
| 4,225,790 A | 9/1980 | Parsons, Jr. et al. |
| 4,323,055 A | 4/1982 | Kubiatowicz |
| 4,423,725 A | 1/1984 | Baran et al. |
| 4,581,017 A | 4/1986 | Sahota |
| 4,588,395 A | 5/1986 | Lemelson |

(List continued on next page.)

FOREIGN PATENT DOCUMENTS

| | | |
|---|---|---|
| DE | 392700 A1 | 2/1991 |

(List continued on next page.)

OTHER PUBLICATIONS

Radiation Quantities and Units, ICRU Report 33, International Commission on Radiation, Units and Measurements, Apr. 15, 1980.

Effects of high–dose intracoronary iradiation on vasomotor function and smooth muscle histopathology, Joseph G. Wiedermann, et al., Interventional Cardiology Center, Department of Medicine and Radiation Oncology and Section of Cardiac Pathology, Columbia–Presbyterian Medical Center and Columbia University, 1994 the American Physiological Society.

(List continued on next page.)

*Primary Examiner*—Samuel G. Gilbert
(74) *Attorney, Agent, or Firm*—Knobbe Martens Olson & Bear, LLP

(57) ABSTRACT

A sealed radiation source, which may be used to deliver a radioactive dose to a site in a body lumen. The source comprises a thin flexible substrate, and a layer of radioisotope attached thereto. The source may further comprise additional layers such as one or more tie layers disposed between the substrate and the radioisotope layer and one or more outer coating layers. In one embodiment, the source is wrapped around an inflatable balloon. Inflation of the balloon at a treatment site positions the source directly adjacent to the vessel wall, and allows irradiation of the site following or simultaneously with a balloon angioplasty, stent implantation, or stent sizing procedure.

47 Claims, 7 Drawing Sheets

U.S. PATENT DOCUMENTS

| | | | |
|---|---|---|---|
| 4,655,771 A | 4/1987 | Wallsten |
| 4,674,480 A | 6/1987 | Lemelson |
| 4,706,652 A | 11/1987 | Horowitz |
| 4,762,129 A | 8/1988 | Bonzel |
| 4,815,449 A | 3/1989 | Horowitz |
| 4,819,618 A | 4/1989 | Liprie |
| 4,878,492 A | 11/1989 | Sinofsky et al. |
| 4,994,013 A | 2/1991 | Suthanthiran et al. |
| 5,011,677 A | 4/1991 | Day et al. |
| 5,019,369 A | 5/1991 | Presant et al. |
| 5,040,548 A | 8/1991 | Yock |
| 5,059,166 A | 10/1991 | Fischell et al. |
| 5,061,273 A | 10/1991 | Yock |
| 5,106,360 A | 4/1992 | Ishiwara et al. |
| 5,152,747 A | 10/1992 | Oliver |
| 5,163,896 A | 11/1992 | Suthanthiran et al. |
| 5,176,617 A | 1/1993 | Fischell et al. |
| 5,199,939 A | 4/1993 | Dake et al. |
| 5,213,561 A | 5/1993 | Weinstein et al. |
| 5,267,960 A | 12/1993 | Hayman et al. |
| 5,302,168 A | 4/1994 | Hess |
| 5,302,369 A | 4/1994 | Day et al. |
| 5,342,283 A | 8/1994 | Good |
| 5,354,257 A | 10/1994 | Roubin et al. |
| 5,411,466 A | 5/1995 | Hess |
| 5,424,288 A | 6/1995 | Order |
| 5,484,384 A | 1/1996 | Fearnot |
| 5,498,227 A | 3/1996 | Mawad |
| 5,503,613 A | 4/1996 | Weinberger |
| 5,540,659 A | 7/1996 | Tierstein |
| 5,605,530 A | 2/1997 | Fischell et al. |
| 5,616,114 A | 4/1997 | Thornton et al. |
| 5,618,266 A | 4/1997 | Liprie |
| 5,643,171 A | 7/1997 | Bradshaw et al. |
| 5,653,683 A | 8/1997 | D'Andrea |
| 5,662,580 A | 9/1997 | Bradshaw et al. |
| 5,674,177 A | 10/1997 | Hehrlein et al. |
| 5,683,345 A | 11/1997 | Waksman et al. |
| 5,688,220 A | 11/1997 | Verin et al. |
| 5,707,332 A | 1/1998 | Weinberger |
| 5,713,828 A | 2/1998 | Coniglione |
| 5,720,717 A | 2/1998 | D'Andrea |
| 5,722,984 A | 3/1998 | Fischell et al. |
| 5,728,042 A | 3/1998 | Schwager |
| 5,730,698 A | 3/1998 | Fischell et al. |
| 5,755,690 A | 5/1998 | Saab |
| 5,762,631 A | 6/1998 | Klein |
| 5,762,903 A | 6/1998 | Park et al. |
| 5,782,740 A | 7/1998 | Schneideman |
| 5,782,741 A | 7/1998 | Bradshaw et al. |
| 5,782,742 A | 7/1998 | Crocker et al. |
| 5,795,286 A | 8/1998 | Fischell et al. |
| 5,840,008 A | 11/1998 | Klein et al. |
| 5,840,009 A | 11/1998 | Fischell et al. |
| 5,860,991 A | 1/1999 | Klein et al. |
| 5,863,284 A | 1/1999 | Klein |
| 5,871,436 A | 2/1999 | Eury |
| 5,879,282 A | 3/1999 | Fischell et al. |
| 5,911,717 A | 6/1999 | Jacobson et al. |
| 5,919,126 A | 7/1999 | Armini |
| 5,980,566 A * | 11/1999 | Alt et al. ............. 623/1 |
| 6,013,019 A | 1/2000 | Fischell et al. |
| 6,019,718 A | 2/2000 | Hektner |
| 6,024,690 A | 2/2000 | Lee et al. |
| 6,033,357 A | 3/2000 | Ciezki et al. |
| 6,042,600 A | 3/2000 | Rosenthal et al. |
| 6,045,495 A | 4/2000 | Weinberger |
| 6,048,299 A | 4/2000 | Hoffmann |
| 6,050,930 A | 4/2000 | Teirstein |
| 6,059,713 A | 5/2000 | Urick et al. |
| 6,059,714 A | 5/2000 | Armini et al. |
| 6,059,752 A | 5/2000 | Segal |
| 6,071,227 A | 6/2000 | Popowski et al. |
| 6,077,413 A | 6/2000 | Hafeli et al. |
| 6,099,457 A * | 8/2000 | Good ................. 600/8 |
| 6,103,295 A | 8/2000 | Chan et al. |
| 6,149,574 A * | 11/2000 | Trauthen et al. ........ 600/3 |
| 6,287,249 B1 * | 9/2001 | Tam et al. ............ 600/3 |
| 6,176,821 B1 | 1/2002 | Crocker et al. |

FOREIGN PATENT DOCUMENTS

| | | |
|---|---|---|
| EP | 0 433 011 B1 | 7/1994 |
| EP | 0 688 580 A1 | 12/1995 |
| EP | 0593 136 B1 | 3/1997 |
| WO | WO 93/04735 | 3/1993 |
| WO | WO 94/23789 | 10/1994 |
| WO | WO 94/26205 | 11/1994 |
| WO | WO 95/19807 | 7/1995 |
| WO | WO 95/29008 | 11/1995 |
| WO | WO 96/10436 | 4/1996 |
| WO | WO 96/13303 | 5/1996 |
| WO | WO 96/14898 | 5/1996 |
| WO | WO 96/22121 | 7/1996 |
| WO | WO 97/18012 | 5/1997 |
| WO | WO 98/33555 | 8/1998 |
| WO | WO 99/24116 | 5/1999 |
| WO | WO 99/32192 | 7/1999 |
| WO | WO 99/42163 | 8/1999 |
| WO | WO 99/42177 | 8/1999 |
| WO | WO 00/29501 | 5/2000 |

OTHER PUBLICATIONS

Intracoronary Irradiation Markedly Reduces Restenosis After Balloon Angioplasty in a Porcine Model, Joseph G. Wiedemann, M.D., et al., JACC vol. 23 No. 6, May 1994; 1491–8.

Intracoronary Irradiation Markedly Reduces Neointimal Proliferation After Balloon Angioplasty in a Swine; Persistent Benefit at 6–Month Follow–up; Joseph G. Wiedemann, M.D., et al., JACC vol. 25 No. 6, May 1995; 1451–6.

Discoveries in Radiation for Restenosis, Emory University of School of Medicine, Presented by The Andreas Gruentzig Cardiovascular Center and the Department of Radiation Oncology of Emory University School of Medicine; J.W. Marriott Hotel at Lenox, Atlanta, GA; Jan. 11–12, 1996.

* cited by examiner

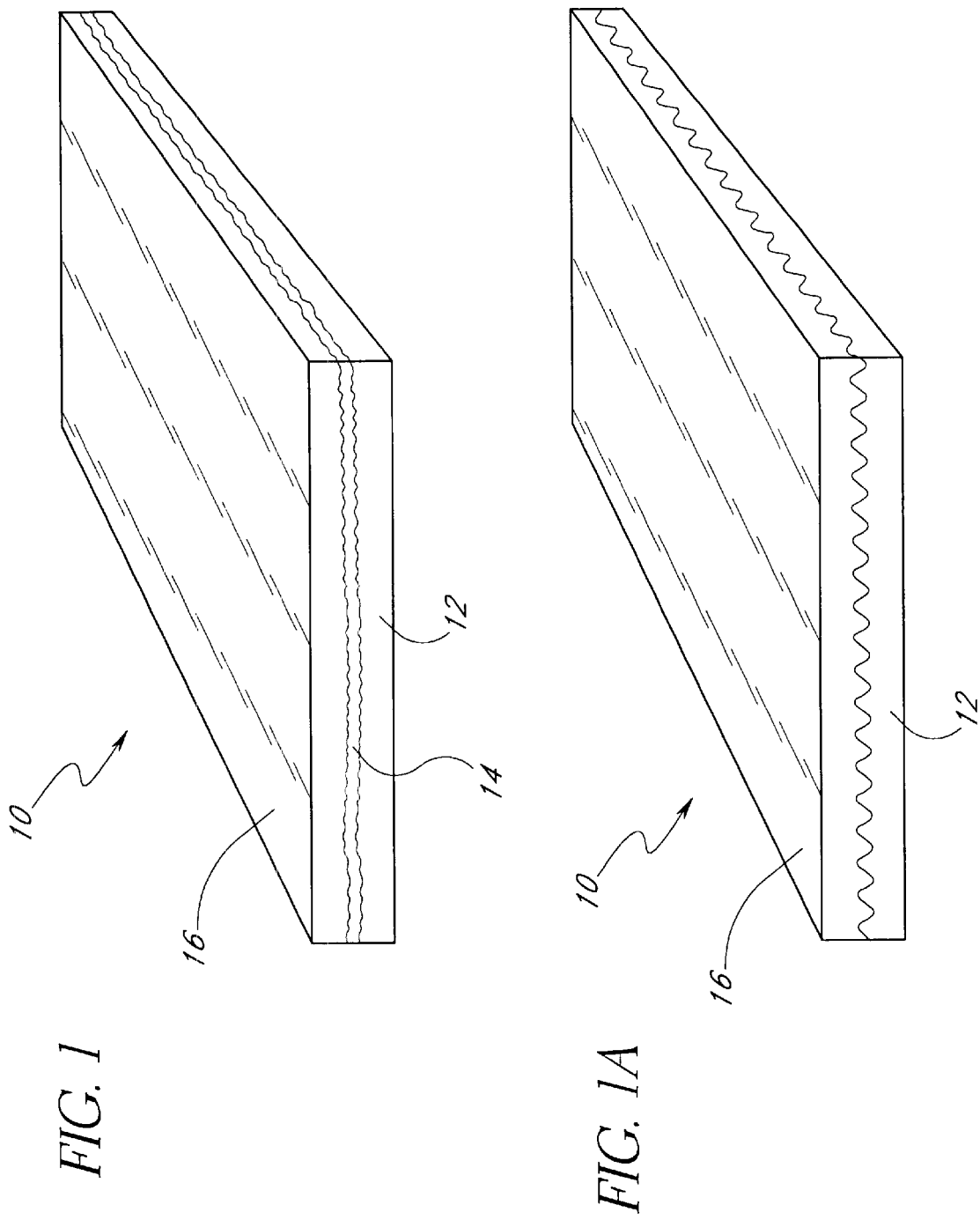

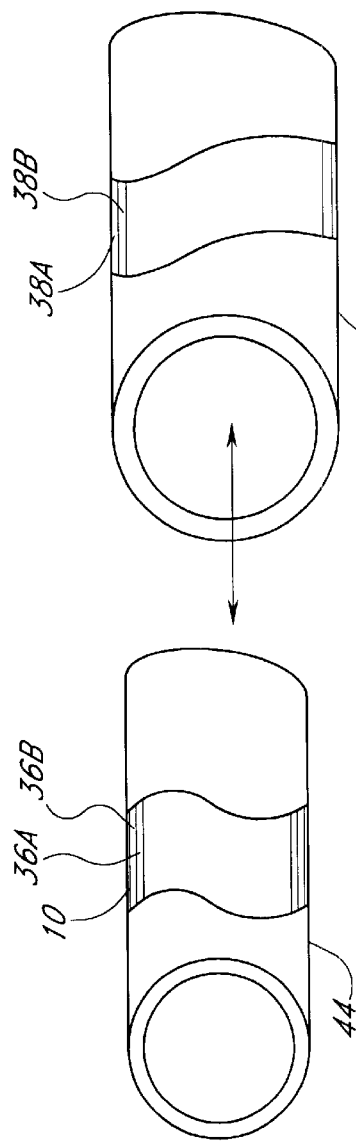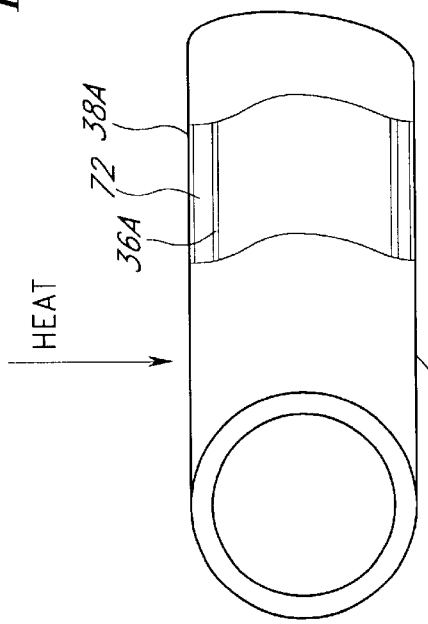

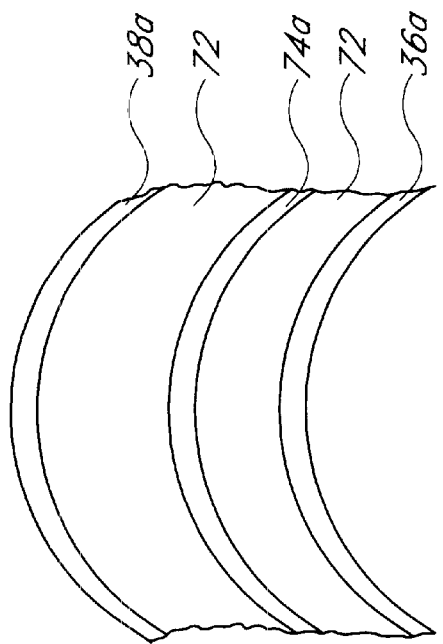
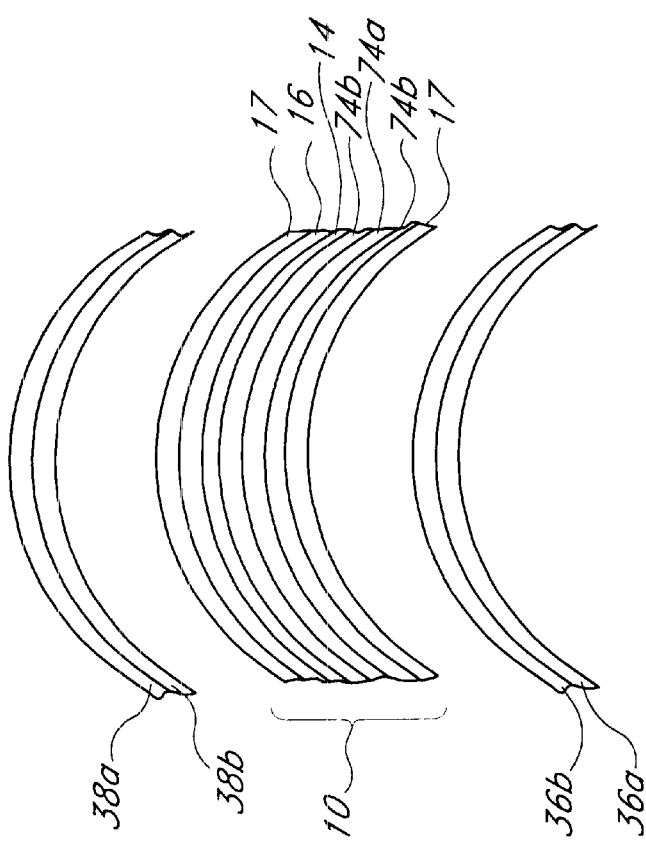

MULTI LAYER RADIATION DELIVERY BALLOON

RELATED APPLICATION DATA

This application is a continuation-in-part of Ser. No. 09/253,433, filed Feb. 19, 1999, abandoned, and a continuation-in-part of Ser. No. 09/256,337, filed Feb. 19, 1999, now U.S. Pat. No. 6,287,249, each of which is a continuation-in-part of Ser. No. 09/025,921, filed Feb. 19, 1998, abandoned. This application is also a continuation-in-part of Ser. No. 09/040,172, filed Mar. 17, 1998, now U.S. Pat. No. 6,149,574.

FIELD OF THE INVENTION

This invention relates to catheters used to deliver radiation to prevent or slow restenosis of an artery traumatized such as by percutaneous transluminal angioplasty (PTA).

BACKGROUND OF THE INVENTION

PTA treatment of the coronary arteries, percutaneous transluminal coronary angioplasty (PTCA), also known as balloon angioplasty, is the predominant treatment for coronary vessel stenosis. Approximately 300,000 procedures were performed in the United States in 1990 and nearly one million procedures worldwide in 1997. The U.S. market constitutes roughly half of the total market for this procedure. The increasing popularity of the PTCA procedure is attributable to its relatively high success rate, and its minimal invasiveness compared with coronary by-pass surgery. Patients treated by PTCA, however, suffer from a high incidence of restenosis, with about 35% or more of all patients requiring repeat PTCA procedures or by-pass surgery, with attendant high cost and added patient risk.

Recent attempts to prevent restenosis by use of drugs, mechanical devices, and other experimental procedures have had limited long term success. Stents, for example, dramatically reduce acute reclosure, and slow the clinical effects of smooth muscle cell proliferation by enlarging the minimum luminal diameter, but otherwise do nothing to prevent the proliferative response to the angioplasty induced injury.

Restenosis is now believed to occur at least in part as a result of injury to the arterial wall during the lumen opening angioplasty procedure. In some patients, the injury initiates a repair response that is characterized by hyperplastic growth of vascular cells in the region traumatized by the angioplasty which is termed neointimal hyperplasia. Neointimal hyperplasia narrows the lumen that was opened by the angioplasty, regardless of the presence of a stent, thereby necessitating a repeat PTCA or other procedure to alleviate the restenosis.

Preliminary studies indicate that intravascular radiotherapy (IVRT) has promise in the prevention or long-term control of restenosis following angioplasty. IVRT may also be used to prevent or delay stenosis following cardiovascular graft procedures or other trauma to the vessel wall. Proper control of the radiation dosage, however, appears to be important to inhibit or arrest hyperplasia without causing excessive damage to healthy tissue. Overdosing of a section of blood vessel can cause arterial necrosis, inflammation, hemorrhaging, and other risks discussed below. Underdosing will result in inadequate inhibition of smooth muscle cell hyperplasia, or even exacerbation of hyperplasia and resulting restenosis.

The prior art contains many examples of catheter based radiation delivery systems. The simplest systems disclose seed train type sources inside closed end tubes. An example of this type of system can be found in U.S. Pat. No. 5,199,939 to Dake. In order to separate the radiation source from the catheter and allow re-use of the source, a delivery system is disclosed by U.S. Pat. No. 5,683,345 to Waksman et al. where radioactive source seeds are hydraulically driven into the lumen of a closed end catheter where they remain for the duration of the treatment, after which they are pumped back into the container. Later disclosures integrated the source wire into catheters more like the type common in interventional cardiology. In this type of device, a closed end lumen, through which is deployed a radioactive source wire, is added to a conventional catheter construction. A balloon is incorporated to help center the source wire in the lumen. It is supposed that the radioactive source wire would be delivered through the catheter with a commercial type afterloader system produced by a manufacturer such as Nucletron, BV. These types of systems are disclosed in Liprie U.S. Pat. No. 5,618,266, Weinberger U.S. Pat. No. 5,503,613, and Bradshaw U.S. Pat. No. 5,662,580.

In the systems disclosed by Dake and Waksman, the source resides in or very near the center of the catheter during treatment. However, it does not necessarily reside in the center of the artery. The systems disclosed by Weinberger and Bradshaw further include a centering mechanism, such as an inflatable balloon, to overcome this shortcoming. In either case, the source activity and energy must be high enough to overcome absorption loss encountered as the particles traverse the lumen of the blood vessel to get to the target tissue site in the vessel wall. Higher activity and energy sources, however, can have undesirable consequences. First, the likelihood of radiation inadvertently affecting untargeted tissue is higher because the absorption factor per unit tissue length is lower. Second, the higher activity and energy sources are more hazardous to the medical staff and thus require additional shielding during storage and additional precaution during use. In addition, the source of any activity or energy may or may not be exactly in the center of the lumen, so the dose calculations are subject to error factors due to non-uniformity in the radial distance from the source surface to the target tissue. The impact of these factors is a common topic of discussion at recent medical conferences addressing Intravascular Radiation Therapy, such as the Trans Catheter Therapeutics conference, the Scripps Symposium on Radiotherapy, the Advances in Cardiovascular Radiation Therapy meeting, the American College of Cardiology meeting, and the American Heart Association Meeting.

The impact on treatment strategy is discussed in detail in a paper discussing a removable seed system similar to the ones disclosed above (Tierstein et al., Catheter based Radiotherapy to Inhibit Restenosis after Coronary Stenting, NEJM 1997; 336(24):1697–1703). Tierstein reports that Scripps Clinic physicians inspect each vessel using ultrasonography to assess the maximum and minimum distances from the source center to the target tissue. To prevent a dose hazard, they will not treat vessels where more than about a 4× differential dose factor (8–30 Gy) exists between the near vessel target and the far vessel target. Differential dose factors such as these are inevitable for a catheter in a curvilinear vessel such as an artery, and will invariably limit the use of radiation and add complexity to the procedure. Moreover, the paper describes the need to keep the source in a lead transport device called a "pig", as well as the fact that the medical staff leaves the catheterization procedure room during the treatment. Thus added complexity, time and risk is added to the procedure caused by variability of the position of the source within the delivery system and by the activity and energy of the source itself.

In response to these dosimetry problems, several more inventions have been disclosed in an attempt to overcome the limitations of the high energy seed based systems. These systems share a common feature in that they attempt to bring the source closer to the target tissue. For example, U.S. Pat. No. 5,302,168 to Hess teaches the use of a radioactive source contained in a flexible carrier with remotely manipulated windows; Fearnot discloses a wire basket construction in U.S. Pat. No. 5,484,384 that can be introduced in a low profile state and then deployed once in place; Hess also purports to disclose a balloon with radioactive sources attached on the surface in U.S. Pat. No. 5,302,168; Hehrlein discloses a balloon catheter coated with an active isotope in WO 96/22121; and Bradshaw discloses a balloon catheter adapted for use with a liquid isotope in U.S. Pat. No. 5,662,580. The purpose of all of these inventions is to place the source closer to the target tissue, thus improving the treatment characteristics of dosimetry.

In a non-catheter based approach, U.S. Pat. No. 5,059,166 to Fischell discloses an IVRT method that relies on a radioactive stent that is permanently implanted in the blood vessel after completion of the lumen opening procedure. Close control of the radiation dose delivered to the patient by means of a permanently implanted stent is difficult to maintain because the dose is entirely determined by the activity of the stent at the particular time it is implanted. In addition, current stents are generally not removable without invasive procedures. The dose delivered to the blood vessel is also non-uniform because the tissue that is in contact with the individual struts of the stent receive a higher dosage than the tissue between the individual struts.

Additional problems arise when conventional methods, such as ion implantation, are used to make a radioactive source for IVRT. Hehrlein describes the use of direct ion implantation of active P-32 in his paper "Pure β-Particle-Emitting Stents Inhibit Neointima Formation in Rabbits" cited previously. While successfully providing a single mode of radiation using this method, the ion implantation process presents other limitations. For example, ion implantation is only about 10 to 30% efficient. In other words, only about one to three of every ten ions put into the accelerator is implanted on the target, and the remainder remains in the machine. Thus, the radiation level of the machine increases steadily with consistent use. With consistent use, the machine can become so radioactive that it must be shut down until the isotope decays away. Therefore, the isotope used must be of a relatively short half-life and/or the amount of radiation utilized in the process must be very small, in order to shorten the "cooling of" period. Moreover, the major portion of the isotope is lost to the process, implying increased cost to the final product.

Another approach to the same set of problems is to use a nuclide suspended in solution to inflate a balloon (Thornton '114). This technique provides uniform nuclide distribution within the balloon to form the source, resulting in uniform dose patterns. Also, this configuration moves the position of the nuclide closer to the target tissue. No special catheter is required for this type of approach, and many nuclides are available in liquid form. Hence, several investigators have begun clinical studies on so called "[radioactive]liquid filled balloons."

While a seemingly adequate solution to the problems of centering and dosimetry, the liquid filled balloon systems have an obvious drawback known to those familiar with the design, manufacture, or use of balloon angioplasty catheters: balloons potentially break. If a balloon is used to contain an active nuclide, a break poses an obvious health threat to the patient, physician and any nearby laboratory personnel. A break or leak may also shut down the procedure room.

In all of the foregoing designs, full containment of the isotope remains a significant challenge. The American National Standards Institute (ANSI) publishes a standard for sealed sources (ANSI N44.1-1973 Integrity and Test Specifications for Selected Brachytherapy Sources), and the US Nuclear Regulatory Commission (NRC) defines a sealed source as containing less than 5 nanoCuries ($5 \times 10^{-9}$ Curies) of removable activity. Hehrlein reported (Scripps Conference, January 1998) a balloon coated with P-32 that lost 0.5% of its contained activity in an animal study. Even with only 1 mCi of contained activity, the balloon proposed by Hehrlein would have lost 5000 nCi, well beyond NRC standards for a sealed source, and well outside of the ANSI definition of a sealed source.

Despite the foregoing, among many other advances in IVRT, there remains a need for an IVRT method and apparatus that delivers an easily controllable uniform dosage of radiation without the need for special devices or methods to center a radiation source in the lumen. Furthermore, a need remains for a radiation delivery device which is similar in use to conventional angioplasty balloon catheters, and which has a sealed source to prevent escape of radioactive species.

SUMMARY OF THE INVENTION

There is provided in accordance with one aspect of the present invention, a multilayer radiation delivery source. The source comprises a first bonding layer, having a first side, a second bonding layer, having a second side which faces toward the first side, and an isotope layer in between the first side and the second side. The first side and the second side are secured together through the isotope layer to produce a multilayer radiation delivery source. In one embodiment, the isotope layer comprises a metal salt or oxide and at least one isotope.

In accordance with another aspect of the invention, there is provided a radiation delivery balloon catheter. The catheter comprises an elongate flexible tubular body, having a proximal end and a distal end. An inflatable balloon is provided on the tubular body near the distal end, and is in fluid communication with an inflation lumen extending axially through the tubular body. A balloon bonding surface is carried on the outer surface of the balloon, and a radiation source is provided on the balloon bonding surface. An encapsulant surrounds the radiation source. The encapsulant has at least an encapsulant bonding surface on its radially inwardly facing surface for fusing with the balloon bonding surface at least proximally and distally of the radiation source.

In accordance with another aspect of the present invention, there is provided a method of treating a site within a vessel. The method comprises the steps of identifying a site in a vessel to be treated, and providing a radiation delivery catheter. The catheter has an expandable balloon with a thin film radiation source thereon. The thin film comprising a substrate layer having an isotope thereon, the isotope encapsulated by an outer encapsulant layer which is fused to the substrate throughout the length of the source. The balloon is positioned within the treatment site and inflated to bring the source in close proximity to the vessel wall. A dose of radiation is delivered from the delivery balloon to the treatment site. The balloon is thereafter deflated and removed from the treatment site.

In accordance with another aspect of the present invention, there is provided a method of simultaneously performing balloon dilation of a stenosis in a body lumen and delivering radian to the body lumen. The method comprises the steps of identifying a stenosis in a body lumen. A treatment catheter is provided, having an elongate flexible tubular body with an inflatable balloon near the distal end. A cylindrical thin film radiation delivery layer is provided on the balloon, and an encapsulant layer is positioned over the radiation delivery layer. A continuous seal is provided between the encapsulant, the radiation delivery layer, and the balloon along at least the length of the radiation delivery layer to provide a sealed source. The balloon is inserted into the lumen, transluminally advanced therethrough, and positioned within the stenosis. The balloon is inflated to radially expand the vessel in the area of the stenosis, and simultaneously deliver radiation from the thin film to and through the vessel wall.

In accordance with another aspect of the present invention, there is provided a method of simultaneously performing balloon dilation of a stenosis in a body lumen, delivering a stent, and delivering radiation to the body lumen. The method comprises the steps of identifying a stenosis in a vessel. A treatment catheter is provided, having an elongate flexible tubular body with an inflatable balloon near the distal end. A cylindrical thin film radiation delivery layer is provided on the balloon, and an encapsulant layer is positioned over the radiation delivery layer. A continuous seal is provided between the encapsulant, the radiation delivery layer, and the balloon along at least the length of the radiation delivery layer to provide a sealed source. The balloon is inserted into the lumen, transluminally advanced therethrough, and positioned within the stenosis. The balloon is inflated to radially expand the vessel in the area of the stenosis, and simultaneously deliver the stent. Radiation is also delivered from the thin film to the vessel wall.

In accordance with a further aspect of the present invention, there is provided a method of manufacturing a sealed source radiation delivery balloon catheter. The method comprises the steps of extruding a tube for producing a balloon, where the tube has a bonding layer on a radially outwardly facing surface thereof. An annular radiation delivery source is positioned or attached adjacent the balloon bonding layer. A tubular encapsulant is extruded, having a sealing layer on a radially inwardly directed surface thereof. The encapsulant is positioned concentrically around the radiation source and the balloon to produce a balloon-source-encapsulant stack, and the stack is exposed to elevated temperature to bond at least one of the balloon and the encapsulant to the source, thereby producing a sealed source.

In accordance with yet another aspect of the present invention, there is provided a multilayer radiation delivery source. The source comprises first, second, and third portions. The first portion comprises a first support layer having a first bonding layer thereon. The second portion comprises a second support layer having a second bonding layer thereon. The third portion comprises an isotope, and lies between the first and second bonding layers. The first and second bonding layers of the source begin to melt at a lower temperature than the first and second support layers.

Further features and advantages of the present invention will become apparent to those of skill in the art in view of the detailed description of preferred embodiments which follow, when considered together with the attached drawings and claims.

BRIEF DESCRIPTION OF THE DRAWINGS

FIG. 1 is a schematic perspective view of a thin film radiation source in accordance with the present invention.

FIG. 1A is a schematic perspective view of an alternate thin film source in accordance with the present invention.

FIG. 8 is a schematic illustration of the assembly of a one embodiment of multi-layered sealed source in which the sections are shown in partial cross-section.

FIG. 9 is an exploded cross-sectional view through a preferred multi-layered sealed source embodiment of the present invention, prior to fusing the bonding layers.

FIG. 9A is a cross-sectional view of the source of FIG. 9 where the bonding layers have been completely fused.

Figure 1B:
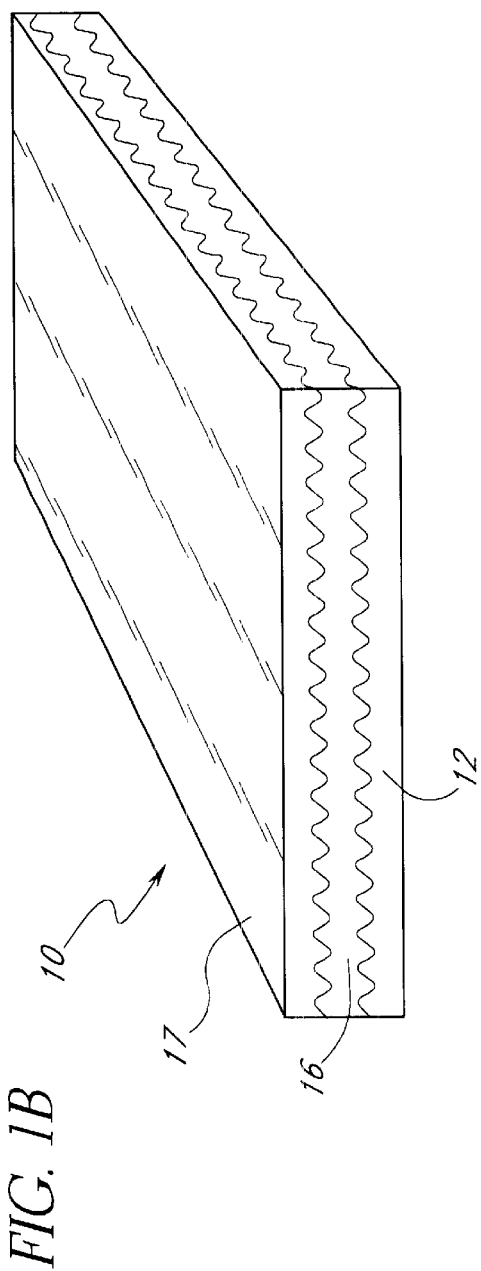
FIG. 1B is a schematic of a cross-section of one embodiment of the radiation delivery source of the present invention having a substrate layer, an isotope layer and a coating layer.

The drawings figures are not necessarily to scale.

DETAILED DESCRIPTION OF THE PREFERRED EMBODIMENT

This invention provides a novel sealed source design, new in terms of structure, materials and production methods. The invention can be generally described as a thin film radioactive source intended for site specific delivery of radiation ("brachytherapy") to an anatomical structure. As presently contemplated, one embodiment of the source design is intended for incorporation into the balloon segment of a vascular dilatation catheter such as that disclosed in U.S. Pat. No. 5,782,742, Crocker, et al., the disclosure of which is incorporated in its entirety herein by reference.

Alternatively, the source could be incorporated into traditional "seeds," or placed on a wire, or on a trocar, or most any other delivery system. The thin film can be rolled up into a cylindrical configuration for insertion and unrolled in-situ for positioning adjacent the vessel wall either by itself or as a laminate on a flexible metal or polymeric support sheet, such as disclosed in U.S. patent application Ser. No. 08/965,900, entitled Radiation Delivery Catheter, filed Nov. 7, 1997 by von Hoffmann, the disclosure of which is incorporated in its entirety herein by reference. However, for the sake of simplicity, the present invention will be described herein primarily in the context of a sealed source balloon structure for use in intravascular procedures.

The term "thin film source" is descriptive of the invention's structure. Referring to FIG. 1, the source 10 comprises of a thin sheet, or "substrate" layer 12, a chemical attachment or "tie" layer 14 for binding the isotope, and an isotope species 16. The substrate 12 can consist of a very thin (1 microns, or from about 0.00004 to about 0.002"thickness) sheet or tubing. At these thicknesses, a wide variety of biologically compatible materials are very flexible and conforming. Examples of substrates commercially available at these thicknesses are Mylar® (polyester), Kapton® (polyimide), polyethylene, nylon, and polyurethane, EMA, and polyethylene terephthalate (PET), in the form of sheet or tubing, or even metal foils.

Figure 1C:
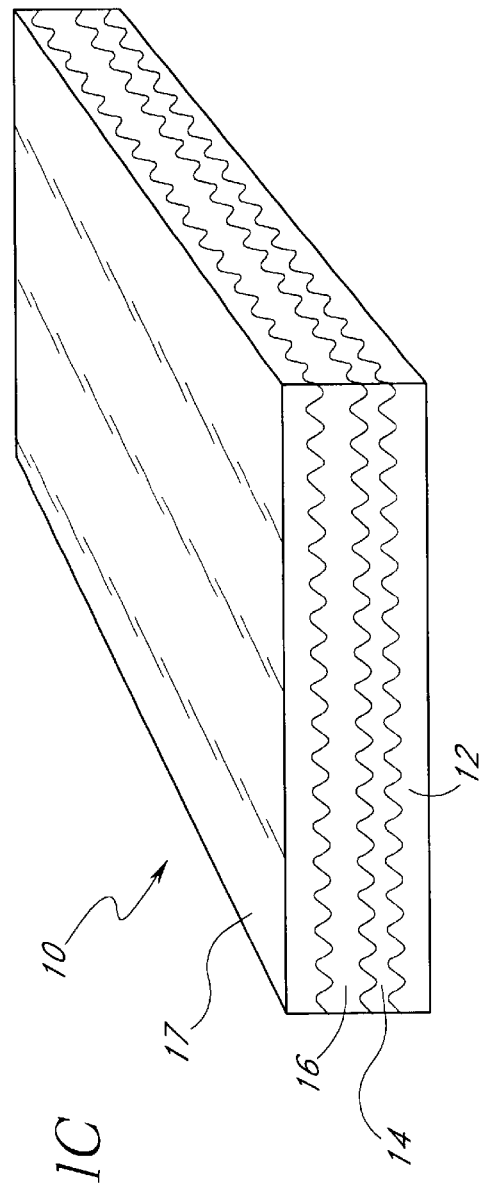
FIG. 1C is a schematic of a cross-section of one embodiment of the radiation delivery source of the present invention having a substrate layer, a tie layer, an isotope layer and a coating layer.

FIGS. 1A–1C show additional embodiments of the thin film source of the present invention. Referring to FIG. 1A, a schematic of a cross-section of a two-layer embodiment of thin film source is shown. The first or innermost layer is the substrate 12, and the second or outer layer is the isotope layer 16.

Referring to FIG. 1B, a schematic of a cross-section of thin film source, wherein the source has three layers, is shown. The first or innermost layer is the substrate 12, the second or middle layer is the isotope layer 16, and the outer layer is the coating layer 17.

Referring to FIG. 1C, a schematic of a cross-section of a four-layer embodiment of the thin film source of the present invention is shown. The four layers are the substrate layer 12, tie layer 14, isotope layer 16, and coating layer 17.

The thin film sources of the present invention are comprised of two or more layers of materials. There may or may not be a clear visual or physical distinction between the various layers in the source 10 because each layer need not be a discrete structural element of the thin film source 10. As the layers bond together to form the source, they may become blended, alloyed, intermingled or the like to form what looks and acts like a single layer having a somewhat heterogeneous composition. For this reason, the various layers as defined and used herein are intended to denote the functional characteristics of the components or help denote what process steps are used in their formation, whether through the use of discrete structural layers or layers blended with neighboring layers, the selection which will be apparent to those of skill in the art in view of the particular materials and components used.

For example, the term tie layer as used herein is intended to denote a functional characteristic which enables securing of the isotope species 16 to the substrate 12, whether through the use of a discrete structural layer (such as an adhesive or functionally analogous component) or a surface modification to the substrate 12 (such as chemical activation), the selection of which will be apparent to those of skill in the art in view of a particular substrate 12 material and isotope layer 16 material. For example, FIG. 1A schematically represents a substrate 12 having an isotope zone 16 comprising at least one isotope.

The thin film sources of the present invention all comprise a substrate layer or substrate 12. The thickness and composition of the substrate layer 12 can be varied widely, depending upon the catheter design or the design of the other medical device to which the isotope species 16 is to be bound. For example, materials in the thickness of conventional PTCA balloons (from about 0.0005 to about 0.005 inches) may be utilized, such as where the balloon itself is used as the substrate 12. Additonally, a layer of bonding material or encapsulant may be used as the substrate 12.

A balloon substrate may be either of the compliant or non-compliant variety, as known in the art. Thus, for a radiation delivery balloon which is not intended to additionally accomplish angioplasty, working pressures on the order of 1 to 5 atmospheres may be used. At such relatively low pressures, a variety of balloon materials may be utilized, which do not experience excessive expansion as a function of pressure. If higher inflation pressures are desired, more traditionally non-compliant materials such as polyethylene terephthalate may be desirable. In general, the radioactive source on the delivery balloon preferably does not expand in response to pressure. The substrate 12 may be polymeric or a metal, depending upon the desired characteristics of the finished product.

The shape of the source is generally dictated by the geometry of the substrate 12. When present, any of the layers described herein, other than the substrate, are disposed over at least one surface of the source, and may be disposed over the entire surface of the source. All layers present in a given embodiment need not cover the same areas of the substrate or the entire surface of the source. In one embodiment, the tie layer and isotope layer cover only a portion of the substrate, and the entire substrate is coated with one or more coating layers.

The thin film sources also all comprise an isotope layer 16. The isotope layer comprises at least one radioactive isotope. Such isotopes are preferably either beta- or gamma-emitting. The composition of the isotope layer may be of a wide variety of possibilities. In one embodiment, the isotope layer comprises a collection of individual isotope ions, atoms, or compounds attached to the layer below, preferably in a relatively even distribution. In another embodiment, the isotope layer comprises a metal salt wherein same or all of one ion of the salt has been replaced by isotope ions (simple or complex). Such a salt-containing isotope layer may be bound directly to the substrate layer 12 or to a tie layer 14, if present. The isotope layer preferably has an isotope density or nuclide density in the range of $10^{10}$–$10^{35}$ atoms/$cm^2$, more preferably about $10^{13}$–$10^{25}$ atoms/$cm^2$ more preferably about $10^{25}$ atoms/$cm^2$ and has a thickness of preferably 25–10,000 Angstroms thick, more preferably about 25–100 Angstroms thick.

As used herein, the term "metal salt" refers to a compound comprised of at least one anion and at least one cation. The anions and cations of the metal salt may be either simple (monatomic) ions such as $Al^{3+}$, $Cl^-$, $Ca^{2+}$, $Zn^{2+}$ and $Ag^+$, or complex (polyatomic) ions such as $PO_4^{3-}$, $O_3^{2-}$, and $WO_4^{2-}$. At least one of the ions in the metal salt should comprise a metal. The term "metal" as used herein means all metals, including, for example, semimetals, alkali metals, and alkaline earth metals. Preferably metals are selected from the transition metals or main group of the Periodic Table of the Elements. The term "metal salt" as used herein in its broadest sense can encompass metal oxides.

The thin film sources of the present invention may further comprise at least one tie layer 14. The tie layer 14 lies between the substrate 12 and isotope layer 16 and may act to increase the tenacity of attachment of the isotope layer 16 to the substrate 12. The tie layer 14 may be any composition or structure which functions to bind the isotope 16 to the substrate 12. The tie layer 14 may comprise adhesives, chemically activated surfaces, mechanical locking structures, a chemical coating layer, or a layer of one or more an organic or inorganic compound. Preferred tie layer materials include metals, alloys, metal salts, alumina and other metal oxides, polyester, polyimide and other polymers. Its chemical composition and structure can be varied, depending on the isotope to be attached. It can be an organic or inorganic material or compound; it must only have the appropriate chemistry to attract and bind the isotope or isotope layer materials. The tie layer may be applied to one or both surfaces of the substrate, depending on factors such as the desired activity, composition or geometry of the finished product. In one embodiment, the tie layer 14 is a layer of metal or metal oxide, and it is 100 to 10,000 Angstroms thick, more preferably 200 to 1000 Angstroms thick.

The thin film sources of the present invention may further comprise one or more coating layers 17, as is discussed in connection with FIGS. 6–7 below. A coating layer 17, can act as a sealing means to protect the isotope layer from mechanical abrasion or other injury which could remove radioisotopes from the isotope layer. Although the isotopes in the sources of the present invention may be sufficiently adherent without the addition of a coating layer, addition of a coating layer may aid in providing sufficient protection for the device to be classified as a sealed radiation source, i.e. one that has less than 5 nCi of removable activity. The coating layer may also provide the additional advantage of sealing or binding the layers of the source together.

The coating may be a metal or plastic. Plastic coating materials are preferably biocompatible, but not excessively biodegradable. Preferred materials include cyanoacrylates, acrylics, ethylene methyl acrylate, ethylene methyl acrylate/acrylic acid (EMA/AA), urethanes, thermal plastic urethane (TPU) polybutyl vinyl chloride (PBDC), polyvinylidene chloride (PVDC, such as Saran®) polyethylene, polyethylene terephthalate, nylon and the like. Likewise, metal coatings can be used as well. If the coating is metal, the metal used is preferably one which is bio-stable. For example, platinum, gold, or titanium may be vapor deposited on the surface to encapsulate the isotope layer.

The foregoing thin film structures offer several advantages over existing source designs. First, the source can conform to almost any shape, unlike conventional seed or solid wire type sources or even a thin metal film. Thus, this type of source is ideal for incorporation into flexible catheter-like delivery systems.

The radioisotopes used in the thin film sources of the present invention may be beta or gamma emitters, or both, and may have any of a wide range of half-lives, both long and short. The particular isotope, or combination of isotopes as well as the concentration of isotopes in the source (which determines the dose), can be chosen by one skilled in the art to serve the needs of a particular application. In a recent paper presented by Howard Amols at the January 1998 Scripps Clinic Conference on Intravascular Radiation Therapy entitled "Choosing the Right Isotope: What's New? Insights into Isotopes or Why Is it so Hard to Find the Ideal Isotope?," the author states that the best isotope choice from the perspective of both physics and dosimetry would be a photon source with an energy greater than 3 MeV and a half-life greater than 7 days. Shirish K. Jani, in a lecture entitled "Does the Perfect Isotope Exist?" at the same conference states that the perfect isotope for vascular brachytherapy would exhibit a low dose gradient, low dose levels to surrounding body tissues, manageable radiation exposure levels around the patient and a long half-life. Iodine-125 (I-125, half-life 60 days) and tungsten-188/rhenium-188 (W/Re-188, half-life 70 days) are candidates to meet these criteria, and also have long half-lives. Thus, these are two preferred radioisotopes for use in the present invention. Phosphorous-32 (P-32, half-life 14.3 days) is also a preferred isotope for use in the present invention.

Preferred radioisotopes are selected from the group of gamma emitters (or x-ray emitters) with energies less than about 300 KeV such as I-125, Pd-103, As-73, Gd-153, or the high-energy beta emitters ($E_{max}$>1.5 meV) including P-32 and W/Re-188, or others as may be deemed suitable for a particular use. The selection of the isotope may be influenced by its chemical and radiation properties, and other isotopes not mentioned herein, but which have properties suitable for a particular application, can be utilized in the present invention. Preferred radioisotopes used in the thin film sources of the present invention may be purchased from Oak Ridge National Laboratory (Oak Ridge, Tenn.), New England Nuclear (NEN) or any other commercial suppliers of radioisotopes.

In accordance with one isotope attachment technique, a thin film substrate is treated with a tie layer composed of a three-dimensional matrix with an ionic compound. The choice of the ionic compound is made to encourage the ion desired to bond within the tie layer. In one embodiment, the three-dimensional matrix is polyvinyl pyrrolidone (PVP) with an ionic compound containing a Br anion. The PVP matrix is commonly used as a carrier for $I_2$ in antimicrobial applications. Direct attachment of the ionic compound would result in layers on the molecular scale. To accomplish attachment, the treated substrate is placed in an ionic solution of I-125 ($Na^{125}I$, a commercially available form of I-125). I-125 anions exchange with $Cl^-$ $Br^-$ anions with less affinity to PVP from the PVP, thus incorporating I-125 into the tie layer and producing a gamma radiation source. A similar system can work alternatively in a solution comprising $^{32}P$-containing ions such as $H_3^{32}PO_4$ (a commercially available form of P-32) to form a beta emitting source.

In one specific embodiment of the present invention, a generally rectangular polyester sheet having a width of about 2 cm, a length of about 3 cm and a thickness of about 12 microns was coated with a PVP ion exchange surface and soaked in a 0.125 wt % I-125 in NaI solution. The resulting source may thereafter be wrapped around a balloon having an inflated diameter of about 3.0 mm and an axial length of about 30 mm. The sheet length of 3 cm would allow the source to be wrapped around the inflated balloon approximately 3 full revolutions. Thus, in this context, sheet length corresponds to the circumferential direction as wrapped around the balloon, and sheet width corresponds to the axial length of the source along the balloon. In this embodiment, the activity of the source would be approximately 110 milliCuries per centimeter length of the substrate sheet. Thus, by providing three full revolutions, a net activity of about 330 milliCuries may be produced. This activity is similar to that disclosed by Teirstein for the Ir-192 (gamma) source used in the Scripps study. Using the present invention, the net activity could conveniently be doubled, for example, by lengthening the substrate sheet to about 6 cm, thereby enabling six revolutions of the substrate around the balloon. This may accomplish a respective reduction in treatment time of 50%.

In cases where adequate activity can be achieved with a single wrap of the source, a thin tube could be used alternatively to the sheet. For example, PET tubing can be commercially obtained with wall thicknesses similar to the sheet material described earlier (0.0003–0.001 inch). The tube construction may allow for simpler assembly, but otherwise it possesses the same properties as the rolled sheet.

In one specific embodiment of the present invention a PE/EMA coextruded, crosslinked and expanded tube was manufactured to a wall thickness of 0.001" to 0.0015" thick. A metal oxide tie layer and metal salt isotope layer was placed on the sheet. The nuclide density of P-32 on the tube was similar to that of a sheet of the same specific surface area. A delivery system may be manufactured in similar fashion to the sheet source with the added benefit of sealing the entire tubular substrate to the encapsulant in addition to the proximal and distal balloon to encapsulant seal.

There are alternative ways of taking advantage of the thin film structural properties, however, without utilizing a chemical attachment system for the isotopes. For example, the radioactive isotope or a salt thereof can be attached directly to the sheet without a distinct tie layer 14 through ion implantation, vapor deposition, or sputtering. Thus, for some techniques, a distinct tie layer 14 is omitted completely. See FIGS. 1A and 1B.

Other methods of direct isotope attachment to the substrate can be considered for metal isotopes. For example, vapor deposition and sputtering can be used to deposit metal isotopes on the substrate. The layers in these processes can be controlled to submicron thicknesses, such that all of the physical/mechanical advantages described in the above paragraphs for chemical attachment systems are maintained: flexibility, ability to adjust activity based on multiple wraps, ability to utilize less active isotopes.

Preferred methods of making the isotope layer of the present invention may begin with either a substrate to be coated or a tie layer to serve as the place of attachment. Preferred methods comprise exposing surfaces to fluids comprising reactants or isotopes.

Such fluids may be gaseous (including plasma and vapor) or liquid (such as solutions), with liquid solutions being preferred. As such, the methods below are described in terms of liquid solutions.

Some preferred methods of making the isotope layer of thin film sources of the present invention comprise, in part, either one or both of the following solution processes: (1) oxidation in an acidic solution to form a metal salt from a metal; and (2) ion exchange wherein ions at or near the surface of the metal salt are exchanged with those present in a solution. The first process is based on differences in oxidation-reduction potentials, and the second process is based on differences in solubility. These processes will be taken in turn.

In the first process, the equilibrium is driven by principles of oxidation-reduction (redox). A metal, in the form of a pure metal or part of an alloy, may be converted to a metal salt when it is placed in solution comprising an oxidizing agent. Many metals, including those in preferred embodiments discussed below, can be readily oxidized in solution to form metal cations, which may then form salts with anions in solution.

Whether or not a particular reaction of an oxidizing agent and a metal will occur spontaneously can be predicted by reference to a standard table of half-cell potentials such as that in *CRC Handbook of Chemistry and Physics*, (CRC Press). If the sum of the potentials of the oxidation half-reaction and the reduction half-reaction is positive, then the reaction will occur spontaneously.

For example, it can be predicted that when silver is added to an acid solution of sodium chlorite, the silver will be oxidized. When added to the solution, sodium chlorite ($NaClO_2$) disproportionates to form hypochlorous acid and chlorine dioxide, which is capable of oxidizing silver as shown below:

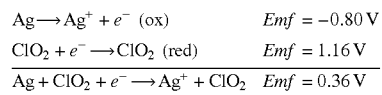

In addition to the reaction shown above, the hypochlorous acid undergoes a redox reaction whereby chloride ions are produced, which then couple with the silver cations to form silver chloride.

The second process is a solubility-driven ion exchange. When, for example, two anions are placed in solution with a given cation, there is a driving force which results in the formation of the metal salt which is less soluble/more insoluble. Because it is difficult to compare solubilities and thus predict behavior when the relative terms "soluble" and "insoluble" are used, solubility is related to a type of equilibrium constant, the solubility product ($K_{sp}$), in order to quantify the degree of solubility for a given compound. The solubility product is equal to the concentrations of the dissociated ions of the salt at equilibrium, that is for salt AB, $K_{sp}=[A^+][B^-]$ wherein $[A^+]$ and $[B^-]$ are the concentrations of the A cation d and the B anion, respectively. If a salt is fairly soluble, the concentrations of its component ions in solution will be relatively high, leading to a relatively large $K_{sp}$. On the other hand, if a salt is fairly insoluble, most of it will be in solid form, leading to low concentrations of the ions and a relatively small $K_{sp}$. Thus, when comparing two salts of the same metal, the salt with the lower $K_{sp}$ is the more insoluble of the two. Solubility products for most common compounds can be found in reference texts such as the *CRC Handbook of Chemistry and Physics* (CRC Press).

The salts silver chloride (AgCl, $K_{sp}=1.77\times10^{-10}$ and silver iodide (AgI, $K_{sp}=8.51\times10^{-17}$) can be used to illustrate the principle of solubility driven ion exchange. The solubility products for these compounds are both fairly low, but $K_{sp}$ for silver iodide is lower by nearly 7 powers of ten, indicating that it is more insoluble than silver chloride. Thus, if solid silver chloride is placed in a solution containing iodide ions, the equilibrium lies on the side of the silver iodide, and the chloride ions will exchange with the iodide ions so that the more insoluble silver iodide is formed. On the other hand, if silver iodide is placed into a solution containing chloride ions, the ion exchange will not take place. In this manner, chloride ions in silver chloride coated on the surface of a substrate can be replaced by $^{125}I$ anions to form a radiation source of the present invention.

The metal salt layer which is the starting point for the above solution ion exchange process may be formed by a redox process such as that described above, or it may be applied directly by means of sputtering, vapor deposition, or other techniques known in the art. Alternatively, if a redox process described above is performed using an oxidizing solution containing a radioisotope, for example $H_3^{32}PO_4$, the radioisotope-containing metal salt layer may be obtained directly, eliminating the need for the ion exchange.

Another preferred method for making thin film sources of the present invention comprises oxidizing a metal, such as those bound to or incorporated in the substrate, and then binding an isotope to the metal oxide. The step in which the metal is oxidized preferably occurs spontaneously in air. Thus, metals such as aluminum and copper, which readily and spontaneously undergo oxidation to form their respective oxides, are preferred. Oxide formation occurs when the metal is exposed to air, but may be enhanced or increased by exposure to oxygen-enriched atmospheres or increased temperature. The binding of the isotope is preferably performed by immersing the metal oxide in a solution containing isotope ions, either simple or complex. The attraction between the metal oxide and the isotope ions is such that the isotope ions will bind to the metal oxide rather than existing free in solution. This binding or "plating" process may occur either with or without displacement of ions from the metal oxide.

There are several advantages to using the processes above to place active isotopes on a source as opposed to the ion implantation of radioisotopes and nuclear bombardment. One advantage is that unwanted isotopes are not formed. As discussed above with reference to Hehrlein '177, neutron activation of a metal-containing source produces numerous isotopes, making it very difficult to control the dose provided by the source.

Another advantage of the present method is that it does not create large quantities of radioactive waste. By using the correct quantity of radioisotope solution, very little waste is produced. Isotopes which are not incorporated into a given source remain in solution and may be used to form another source. Unlike radioactive ion implantation, there is no stray isotope-filled machine chamber that must be cleaned and safely discarded or taken out of use and allowed to "cool."

Yet another advantage of the present method is that it allows use of isotopes which cannot be readily obtained on a solid source by the other means known in the art. With the proper choice of materials and solutions and the disclosure herein, one skilled in the art would be able to create a reaction scheme to make a salt containing most any of the desirable therapeutic radioisotopes. Furthermore, by using particular long-lived isotopes, a radiation source with a longer half-life can be produced that is capable of delivering a dose with less variation between maximum and minimum. Use of an isotope with a longer half-life may provide for a radiation source which is capable of lowering the amount of radioactivity necessary to perform its function over that which incorporates a short-lived isotope.

Another advantage of the present invention is that the radioisotopes are held by strong atomic-level bonding interactions, and which are highly resistant to leaching or release under physiological conditions or during handling. Additionally, the use of ionic bonding is especially useful for radioisotope species such as iodine-125, as the salt form holds the normally volatile iodine atoms in place.

Another benefit to the solution processes of the present invention is that the density of activity of a given isotope or multiple isotopes may be controlled by simply controlling the time of immersion and/or the density and amount of metal salt or tie layer on the source.

Another advantage of the thin film source is that the structure lends itself to batch processing. The coating step can be done in relatively large volumes using common chemical attachment techniques found in the photographic film and semiconductor industries. Radioactive isotopes are commonly provided in solutions, so the final production step of adding the isotope may be as simple as soaking the coated substrate in the isotope solution. This can be simply performed in very small or very large sheet sizes. The ability to perform this step in small batches is advantageous because the amount of radiation in process can be adjusted to suit the radiation capabilities of the manufacturer.

The basic method, as discussed in part above, comprises providing a substrate and forming a coating comprising an insoluble metal salt with at least one radioactive isotope species thereon.

One preferred embodiment of thin film source of the present invention is that which has an isotope layer comprising the gamma-emitting isotope $^{125}I$. As mentioned previously, $^{125}I$ meets the criteria of an "ideal" isotope as defined by Amols and Jani. One method for making a thin film source having an isotope layer comprising $^{125}I$ is that which uses both solution methods discussed above. First, a substrate is provided that comprises silver or elemental silver is attached to the surface of the substrate using well-known methods such as ion implantation, vapor deposition, sputtering, electroplating, or rolling. The silver is then converted to silver chloride (AgCl) via an oxidation-reduction solution process such as that described above which uses an acidic solution of sodium chlorite to reduce the silver and produce silver chloride. Then the silver chloride-coated source is immersed in an ion exchange solution comprising sodium iodide in the form of $Na^{125}I$, wherein the AgCl is converted to $Ag^{125}I$ on the surface of the source. This manufacturing process may be performed quickly, easily and efficiently. In addition, the I-125 with a half-life of 60 days would provide an equivalent or lower dose of radiotherapy for a longer period of time.

As an alternative to the above method, silver chloride could be directly deposited to the surface of the thin film source by means of vapor deposition or other method known in the art, and then immersed in the ion exchange solution containing $Na^{125}I$.

In one specific embodiment of the present invention, a silver foil having a surface area of 4 $cm^2$ was immersed in a solution of 6M HCl and 1M $NaClO_2$ in a 10:1 ratio. A portion of the silver was thereby converted to silver chloride. The foil was then immersed in a bath having about 2 ml of a solution. The solution in the bath contained about 0.07% $Na^{125}I$ in NaI, and was prepared by dissolving 0.5 mg NaI in 2 ml water and adding 4.6 mCi $^{125}I$ into the solution. Following immersion, the resulting activity of the foil was measured at 2 mCi, which, when the amount of carrier (non-radioactive) iodine is factored in, corresponds to about $10_{18}$ atoms of iodine attached to the sheet. In a carrier free solution, this number of I-125 ions would result in an activity of 3 Ci per 4 $cm^2$ of substrate.

Another preferred embodiment of thin film source of the present invention is that which has an isotope layer comprising $^{32}P$. A thin film source having an isotope layer comprising $^{32}P$ can be made by methods similar to that described above for $^{125}I$ using P-32 in the form of orthophosphoric acid ($H_3^{32}PO_4$). First, a substrate is provided. The substrate may be manufactured to contain zinc or a zinc alloy, or the substrate may be coated with zinc or a zinc alloy by vapor deposition or other methods known in the art. The zinc is then converted to a salt such as zinc fluoride ($ZnF_2$, $K_{sp}=3.04\times10^{-2}$) via an oxidation-reduction process similar to that discussed above. The source is then activated by immersing the zinc fluoride-coated source in a solution containing phosphate ion in the form of $^{32}PO_4^{3-}$ or a soluble phosphate salt, whereby the more soluble fluoride ion is exchanged for phosphate to form zinc phosphate ($Zn_3(PO_4)_2$, $K_{sp}=5\times10^{-36}$).

Alternatively, the substrate may be directly coated with zinc fluoride or other similarly insoluble salt by vapor deposition or other means known in the art, and then placed in an ion exchange solution. Another alternative is to use a solution containing $H_3^{32}PO_4$ in the oxidation step so that the zinc is directly converted to zinc phosphate containing the radioisotope, thus eliminating the ion-exchange step. Yet another alternative is to deposit or form calcium fluoride ($CaF_2$, $K_{sp}=1.61\times10^{-10}$) and then expose this to a source of phosphate (orthophosphate) such as $H_3^{32}PO_4$ or $Na_3^{32}PO_4$.

There is an additional advantage to using zinc phosphate in the isotope layer. Zinc phosphate is a stable molecule and is often used in the automotive industry for paint adhesion to galvanized steel. Zinc phosphate has anticorrosive characteristics of its own, and has been used in the past to increase the corrosion resistance of steel. A zinc phosphate coating on a source made of steel, such as a wire or seed, may be an advantage to the source even in the case that it is not used as a radiation delivery device.

Yet another preferred embodiment of thin film source of the present invention is that which has an isotope layer comprising tungsten-188 (W-188 or $^{188}$W) Tungsten-188 undergoes beta decay to become rhenium-188 (Re-188 or $^{188}$Re). Rheniumn-188 undergoes beta decay as well, but emits a much higher energy particle than in W-188 decay. The W-188 has a much longer half-life than does Re-188, thus the W-188 almost continuously creates more Re-188. This process is known as "generator," and these generator isotopes are referred to together by the shorthand W/Re-188 to indicate the relationship between the species. Generators are attractive for use in radiation delivery devices because they combine the energy levels of a short half-life species with the durability of the long half-life species. It is a general rule that particle energy and half-life are inversely proportional, and that long half-life species are more economical and practical to work with than short half-life species.

W/Re-188 is a beta emitting isotope with an energy about 10% higher than P-32. Where I-125 was discussed as a highly favorable gamma emitting isotope, W/Re-188 fits the criteria of both Amols and Jani for a highly favorable beta emitting species for IVRT. The advantage of the W/Re-188 source would be that the source would provide a dose which could be consistently administered over a long period of time. The half-life of W-188 is 70 days as compared to 14 days for the P-32. This represents a consistent dose rate as Re-188, itself a beta emitting isotope, is being produced by the decay of tungsten for a longer period of time.

Tungsten, in the form of tungstate ion ($WO_4^{2-}$) may be readily attached to an oxidized aluminum surface to produce a W/Re-188-containing thin film source of the present invention. An aluminum oxide surface may be attached to the source by sputtering $Al_2O_3$, or Al can be attached by implantation or deposition, followed by an oxidation step. Ambient environment will facilitate the formation of $Al_2O_3$ from aluminum which can be accelerated by increasing the temperature and/or using an oxygen-rich atmosphere. The aluminum oxide surface may then be immersed in a tungstate containing solution, such as an acidic solution of sodium tungstate ($Na_2^{188}WO_4$), in order to attach the W-188 to the alumina surface.

Tungsten may also be applied together with a phosphate in a manner similar to that disclosed by Larsen in U.S. Pat. No. 5,550,006, which is hereby incorporated into the present disclosure by this reference thereto. The method disclosed in Larsen is claimed for use in increasing adhesion of organic resists for printed circuits. The method was used to perform a phosphate conversion coating onto copper. This method may find its application in the radiation delivery device of the present invention in that many polymers and metals other than copper may be coated with this solution. In this method, phosphate may be in the form of $^{32}PO_4^{3-}$, tungstate may be in the form of $^{188}WO_4^{2-}$, or any combination of the isotopes in radioactive or stable form may be used.

Sources employing combinations of various isotopes provide another preferred embodiment in that beta-emitting isotopes may be combined with gamma-emitting isotopes where gamma isotopes can deliver dosage to greater depths.

Thin film sources comprising other metals, metal salts, and isotopes can be made by procedures similar or analogous to the preferred embodiments disclosed above, using materials appropriate for the chemistry of the isotope to be included, as can be determined by one skilled in the art in view of the disclosure herein.

In some embodiments of the thin film source of the present invention, it may be desirable to provide a tie layer, onto which the isotope layer will be placed. The tie layer may comprise adhesives, chemically activated surfaces, a chemical coating layer, or an organic or inorganic compound. Preferred tie layer materials include metals, alloys, metal salts, metal oxides, PVP, and other polymeric materials.

For some polymeric tie layers, the nature of the tie layer 14 will depend on the isotope to be attached. Many different coatings and attachment technologies are available, and new ones can be developed as applications are developed. For example, Iodine-125 (I-125) can be bound to the substrate by passing it over a substrate coated with a polyvinyl pyrrolidone (PVP) as discussed previously. Other preferred polymeric-type tie layers comprise polymeric materials such as polyesters and polyamides.

Another preferred type of tie layer is the metal-type that which comprises a thin layer of metal, metal oxide, metal salt, or alloy. Depending upon the composition of the other layers and materials in the source, depositing a metal-type tie layer may allow an "alloying" process to take place between the metal of the tie layer and any metals present in the isotope layer. This may serve to enhance the tenacity of attachment of the metal salt, and hence the isotope. This may also occur if the tie layer comprises more than one metal or if more than one tie layer is used in making the source. Alloying of this type is common in the semiconductor industry, wherein a chromium layer is used as an initial layer in the deposition of gold. The chromium is alloyed with the gold in order to increase the strength at which the gold is bound to the substrate. If, for example, the isotope layer comprises a zinc salt, a metal such as copper or aluminum may be used as the tie layer. The tie layer may also be in the form of an oxide, such as alumina ($Al_2O_3$) which may aid attachment by providing oxygen to chemically bind the atoms of the metal salt layer thereby increasing the tenacity of attachment. In one embodiment of source, alumina is deposited on a substrate upon which is placed calcium fluoride. The calcium fluoride may then undergo isotope exchange with a source of radioactive phosphate to form a P-32 based thin film source.

A metal-type layer to which the isotope layer is attached may comprise any suitable metal, metal oxide, metal salt or alloy. The layer may be deposited by vapor deposition, sputtering, ion plating, ion implantation, electrodeposition, or other method. When the tie layer is present, there may or may not be a clear distinction between the tie layer and the isotope layer. In performing its function, and depending on the chemistry of the materials involved, the tie layer may become blended, alloyed or intermingled with the isotope layer, thus blurring the lines between the layers. For many of the same reasons, the distinction between the tie layer and a metal-containing substrate layer may also be blurred. In these cases, the term tie layer is meant to be a functional or process-defining definition, rather than a reference to a physically distinct layer of the thin film source.

In another type of system that can be constructed, the tie layer 14 can incorporate a metal exchange surface, which will attach Pd-103 in the form of palladium metal drawn directly from solution. For example, the substrate layer, made from polyimide as disclosed previously, can be coated with reactive metals such as copper, aluminum, or chromium using commonly available techniques such as vapor deposition or sputtering. The coated substrate is then placed in a solution containing the isotope. The difference in oxidation-reduction (redox) potential between the coating metal and the isotope causes the isotope to deposit on the surface of the substrate film. This system can also be used to attach W-188 from a solution of tungsten salts or other metal salt isotopes as well.

Metal isotope species, such as Palladium-103 (Pd-103) or Tungsten/Rhenium-188 (W/Re-188) or Gd-153 can be attached by incorporating a chelating agent onto the polymer substrate, and then soaking the sheet in a solution of Palladium salts, Tungsten salts or Gadolinium salts. These types of chemical technologies can be incorporated into the source design described herein.

An experiment was done to test the effectiveness of using a copper tie layer to enhance the attachment of zinc fluoride onto a Mylar® sheet. A layer of $ZnF_2$ was placed on a first sheet of Mylar by vapor deposition. On a second sheet of Mylar, a layer of copper was placed by vapor deposition, followed by deposition of a layer of $ZnF_2$. The sheets were each placed into solutions of $H_3{}^{32}PO_4$ having similar activities and allowed to react for several hours. The P-32 activity was counted via scintillation counting. It was found that the sheet having the copper tie layer resulted in a greater adsorption of P-32: 71.6% for $Cu/ZnF_2$ vs. 56% for $ZnF_2$ after 1 hour; and 98.4% for $Cu/ZnF_2$ vs. 86% for $ZnF_2$ after 24 hours. Thus, after a significant period of time, the copper tie layer appears to promote and maintain adherence of the zinc salt to the Mylar surface, and can result in a source which has significantly more activity and adhesion than that without the copper tie layer.

Although the sources of the present invention may have isotopes which are sufficiently adherent without further treatment, in some embodiments of the present invention, it may be desirable to place an outer coating on the thin film source. An outer coating can provide further advantages for the thin film source of the present invention in that the coating can help provide additional means to bind the layers of the source together. Perhaps more importantly, an outer coating can increase the abrasion resistance of the source.

Sealed radioactive sources are those which have less than 5 nCi of removable activity. By providing a coating on the source which covers at least the isotope layer, the source can be protected from unwanted loss of activity due to mechanical abrasion of the surface of the source. This may be important, both for providing safe devices for the patient which leave radioisotopes behind only where they are desired, and for monitoring dosage to ensure that the dose which is to be provided by a source will actually reach the treatment site, and not be significantly diminished due to loss of isotope from abrasion which may occur during implantation. It also helps insure that, once the source is positioned for treatment, the radioisotopes will remain at that site and not be washed downstream.

Coating materials are preferably biocompatible, but not excessively biodegradable. Preferred materials include polymeric materials including cyanoacrylates (Loctite, Hartford, Conn.), acrylics, ethylene methyl acrylate (Exxon Chemical Co., Houston, Tex.), ethylene methyl acrylate/acrylic acid (EMA/AA) (Exxon Chemical Co., Houston, Tex.), urethanes and thermal plastic urethane (TPU) (BF Goodrich, Richfield, Ohio), PVDC, PBVC, PE, PET, and combinations thereof. Other preferred coatings may comprise other biocompatible materials, drugs or similar compounds, such as heparin. Many methods are available to perform the coating process, such as dip or immersion coating, spray coating, spin coating, gravure or shrink wrap tubing. If curing is required, the curing technique may be any of the various techniques available, such as air, heat, or UV. Preferably the thickness of the coating which is formed is 1 $\mu$m to 30 $\mu$m more preferably 10 $\mu$m to 20 $\mu$m.

One preferred embodiment of the present invention has a coating that is formed with cyanoacrylate. Another preferred coating layer is that formed by ethylene methyl acrylate/acrylic acid (EMA/AA) polymer. An aqueous dispersion of this coating material, preferably having a viscosity less than 100 centipoise, allows for use of any of the above-mentioned coating methods. UV curable polyurethane acrylate is also useful as a coating layer material. Yet another preferred coating layer is that formed by SARAN. Such a layer may be formed, for example, by immersing the source or a portion thereof into a melt of SARAN or a solution containing SARAN.

The coating layer may also be formed by a spin coating process. Spin coating the thin film source finds advantage in the flexibility to use coating materials having a wide range of viscosities. Low viscosity liquids may be spun on slowly, while a higher viscosity liquid may be spun at a higher velocity to maintain a thin coating. The substrate may be held in place by fixturing or by vacuum during the spin coating process. In an experiment, a dispersion of cyanoacrylate in acetone was dispensed on top of the metal salt surface while the substrate was rotated at 8000 rpm for five minutes. The resulting thickness of the coating was about 6.5 $\mu$m (0.00025 inch). When this specimen, having the spin-coated surface curable coating of cyanoacrylate was extracted in saline for 8 hours at 50° C., the amount of radioactivity extracted was negligible.

In another experiment, two sources were tested to demonstrate the effectiveness of the coating layer by measuring the amount of removable isotope on coated and uncoated sources. Both sources comprised a Mylar thin film substrate and a $ZnF_2/Zn_3({}^{32}PO_4)_2$ isotope layer, with the coated source further comprising a cyanoacrylate coating layer made by dip coating an uncoated source. The test was performed on each source by wiping it with a cotton swap three times on each side. The activity of the swab was measured by scintillation counting. It was found that the amount of removable activity on the uncoated Mylar-based source was 6.76%, while on the coated source the removable activity was merely 0.050%.

In making some embodiments of the thin film source of the present invention, it may be desired that one or more portions of the source or substrate are not covered or coated by particular layers or portions of layers. In such embodiments, the source may be made by the use of masking techniques. In such a technique, the portions of the source or substrate which are to be left alone for a particular step or steps are covered with a piece of a material to serve as the mask. The other portions not covered by the mask are treated (reacted, coated) and then the mask is removed. For example, it may be preferred to have a small border of substrate surrounding the portion of the source onto which the isotope layer is placed. Such an arrangement may be preferred to reduce coating of the side surfaces of the substrate by the isotope layer, reduce edge effects or to enable several distinct and separate sources to be prepared on a single sheet of substrate having spaces therebetween which are not coated by isotope to that the individual sources may be separated once they are completely prepared without the risk of radioactive contamination of the blade or other implement which is used to cut or separate the individual sources.

In one embodiment, a plurality of sources comprising a Mylar substrate, alumina tie layer and $CaF_2/^{32}PO_4$ isotope layer are made using a mask. In this method, the Mylar sheet is placed between a plate and a mask. The plate may be formed of glass, metal or other suitable material. The mask is a stainless steel sheet from which several rectangular-shaped portions have been removed. The three pieces (plate, Mylar, mask) are secured together and then placed in a chamber. Alumina, which forms the tie layer, is then deposited on the rectangular-shaped portions of the Mylar which have been left exposed by the mask. Calcium fluoride is then deposited on the alumina. The mask is then removed, and the entire sheet placed in an ion-exchange bath containing $^{32}PO_4^{3-}$ ions to complete formation of the isotope layer. One or more outer coating layers may optionally be placed on the sheet prior to separation of the individual sources. The sources may also be coated individually following separation, such as following incorporation onto a balloon catheter.

The masking technique is described above in terms of making sources having a border of substrate surrounding an active area comprising a tie layer and isotope layer coating the substrate. Although described as such, the masking technique or variations thereof as would be apparent to one skilled in the art, may be used for other purposes in making the sources of the present invention, such as placing a coating layer on selected portions of the source, and placing different tie layers on different portions of the source.

Figure 2:
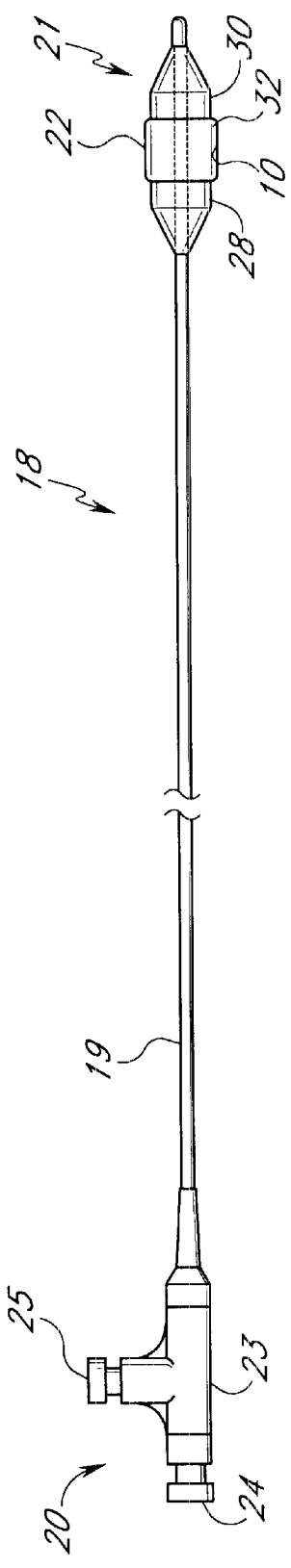
FIG. 2 is a schematic side elevational view of a catheter incorporating the thin film source of the present invention.

Referring to FIG. 2, there is disclosed a radiation delivery catheter 18 incorporating the thin film source 10 in accordance with one aspect of the present invention. Although the description below is primarily directed to the radiation aspect of the invention, catheters embodying additional features known in the vascular dilatation art, such as carrying implantable stents, drug delivery, perfusion and dilatation features, or any combination of these features, can be used in combination with the balloon of the present invention as will be readily apparent to one of skill in the art in view of the disclosure herein.

The catheter 18 generally comprises an elongate tubular body 19 extending between a proximal control end 20 and a distal functional end 21. The length of the tubular body 19 depends upon the desired application. For example, lengths in the area of about 130 cm to about 150 cm are typical for use in radiation delivery by way of a femoral access following or during percutaneous transluminal coronary angioplasty.

The tubular body 19 may be produced in accordance with any of a variety of known techniques for manufacturing balloon-tipped catheter bodies, such as by extrusion of appropriate biocompatible plastic materials. Alternatively, at least a portion or all of the length of tubular body 19 may comprise a spring coil, solid walled hypodermic needle tubing, or braided reinforced wall, as is understood in the catheter and guide wire arts.

In general, tubular body 19, in accordance with the present invention, is provided with a generally circular exterior cross-sectional configuration having an external diameter with the range of from about 0.02 inches to about 0.065 inches. In accordance with one preferred embodiment of the invention, the tubular body 19 has an external diameter of about 0.042 inches (3.2 F.) throughout most of its length for use in coronary applications. Alternatively, generally triangular or oval cross-sectional configurations can also be used, as well as other noncircular configurations, depending upon the number of lumens extending through the catheter, the method of manufacture and the intended use.

In a catheter intended for peripheral vascular applications, the tubular body 19 will typically have an outside diameter within the range of from about 0.039 inches to about 0.085 inches. Diameters outside of the preferred ranges may also be used, provided that the functional consequences of the diameter are acceptable for the intended purpose of the catheter. For example, the lower limit of the diameter for tubular body 19 in a given application will be a function of the number of fluid or other functional lumens, support structures and the like contained in the catheter, and the desired structural integrity.

In general, the dimensions of the catheter shaft and balloon can be optimized by persons of skill in the art in view of the present disclosure to suit any of a wide variety of applications. For example, the balloon of the present invention can be used to deliver radiation to large and small arteries and veins, as well as other lumens, potential spaces, hollow organs and surgically created pathways. The present inventor contemplates radiation delivery to the esophagus, trachea, urethra, ureters, fallopian tubes, intestines, colon, and any other location accessible by catheter which may benefit from radiation delivery. This includes surgically created lumens such as, for example, transjugular intrahepatic portosystemic shunts and others which will be recognized by those of skill in the art. Thus, although the present invention will be described herein primarily in terms of coronary artery applications, it is understood that this is for illustrative purposes only, and the present invention has much broader applicability in the field of radiation delivery.

Tubular body 19 must have sufficient structural integrity (e.g., "pushability") to permit the catheter to be advanced to a treatment site such as distal arterial locations without buckling or undesirable bending of the tubular body 19. Larger diameters generally have sufficient internal flow properties and structural integrity, but reduce perfusion in the artery in which the catheter is placed. Larger diameter catheter bodies also tend to exhibit reduced flexibility, which can be disadvantageous in applications requiring placement of the distal end of the catheter in a remote vascular location. In addition, lesions requiring treatment are sometimes located in particularly small diameter arteries, necessitating the lowest possible profile.

As illustrated schematically in FIG. 2, the distal end 21 of catheter 18 is provided with at least one inflatable balloon 22. The proximal end 20 of catheter 18 is provided with a manifold 23 which may have one or more access ports, as is known in the art. Generally, manifold 23 is provided with a guide wire port 24 in an over the wire embodiment and a balloon inflation port 25. Additional access ports are provided as needed, depending upon the functional capabilities of the catheter 18.

The balloon 22 can also be mounted on a rapid exchange type catheter, in which the proximal guidewire port 24 would not appear on the manifold 23 as is understood in the art. In a rapid exchange embodiment, the proximal guidewire access port 24 is positioned along the length of the tubular body 19, such as between about 1 and about 20 cm from the distal end of the catheter.

Referring to the embodiment of the balloon illustrated in FIG. 2, an enlarged zone 32 is positioned between a proximal reference zone 28 and a distal reference zone 30. The relative lengths of each of the three zones may vary considerably depending upon the intended use of the balloon. In general, suitable dimensions of the balloon, both in terms of diameters and lengths, as well as other catheter dimensions, are disclosed in U.S. Pat. No. 5,470,313 to Crocker, et al., entitled Variable Diameter Balloon Dilatation Catheter, the disclosure of which is incorporated in its entirety herein by reference.

In one particular substantially noncompliant balloon application, the central zone 32 has an axial length of about 25 mm, and each of the proximal zone 28 and distal zone 30 have an axial length of about 5 mm. At an inflation pressure of about 8 atmospheres, the proximal zone 28 has an outside diameter of about 3 mm, and the central zone 32 has an outside diameter of about 3.4 mm. The same balloon at 18 atmospheres inflation pressure has an outside diameter of about 3.1 mm in the proximal zone 28 and an outside diameter of about 3.5 mm in the central zone 32. That particular balloon was constructed from PET, having a wall thickness of about 0.0006 to about 0.0008 inches.

Figure 3:
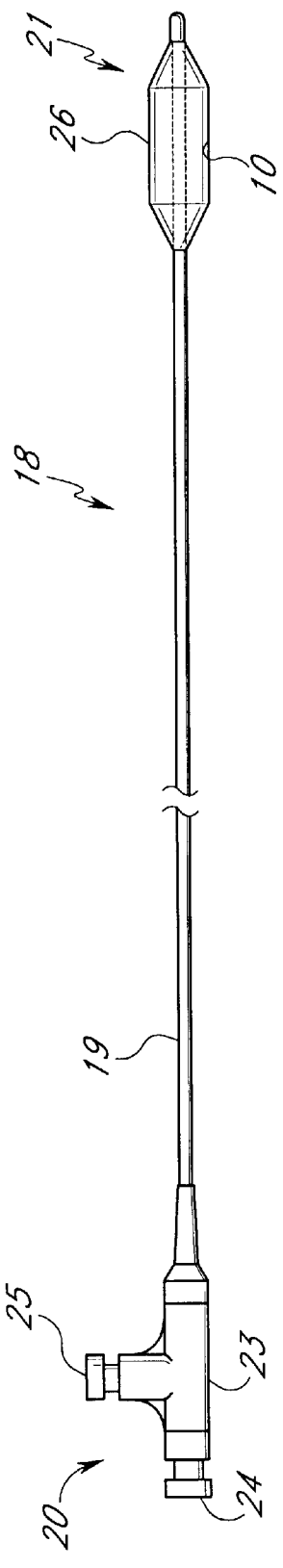
FIG. 3 is a schematic side elevational view of an alternate catheter incorporating the thin film source of the present invention.

In accordance with an alternative embodiment of the balloon of the present invention, illustrated in FIG. 3, the balloon 26 has a generally cylindrical inflated profile throughout its axial working length such as with conventional PTCA balloons. Either the stepped balloon of FIG. 2 or the cylindrical balloon of FIG. 3 can be readily provided with the radiation source 10 discussed below in accordance with the present invention.

The overall dimensions of any particular balloon 22 or 26 will be governed by the intended use, as will be well understood to those of ordinary skill in the art. For example, balloons can be inflatable to a diameter of anywhere within the range of from about 1.5 mm to about 10 mm. For coronary vascular applications, the central zone 32 or overall balloon 26 will normally be inflatable to a diameter within the range of from about 1.5 mm to about 4 mm, with balloons available at about every 0.25 mm increment in between.

The proximal zone 28 and distal zone 30 are generally inflatable to a diameter within the range of from about 1.25 mm to about 9.5 mm. For coronary vascular applications, the proximal and distal zones 28, 30 are preferably inflatable to a diameter within the range of from about 1.25 mm to about 3.5 mm.

The axial length of the central section 32 can be varied considerably, depending upon the desired radiation delivery length as will become apparent. For example, the axial length of the central section 32 may be anywhere within the range of from about 0.5 cm to about 5.0 cm or longer. For coronary vascular applications, the axial length of the central section 32 will normally be within the range of from about 0.5 cm to about 2.0 cm, if the balloon is designed to deliver radiation as well as simultaneously perform conventional PTCA. In a radiation delivery balloon which is not intended to perform PTCA, the axial length of the central zone 32 may exceed the typical length of the lesion, and, in coronary vascular applications, the axial length may be within the range of from about 0.5 cm to about 5 cm or longer.

The axial length of the proximal zone 28 and distal zone 30 may also be varied considerably, depending upon the desired performance characteristics. In general, axial lengths of the cylindrical portion of the proximal zone 28 and distal zone 30 of at least about 3 mm appear useful.

Figure 4:
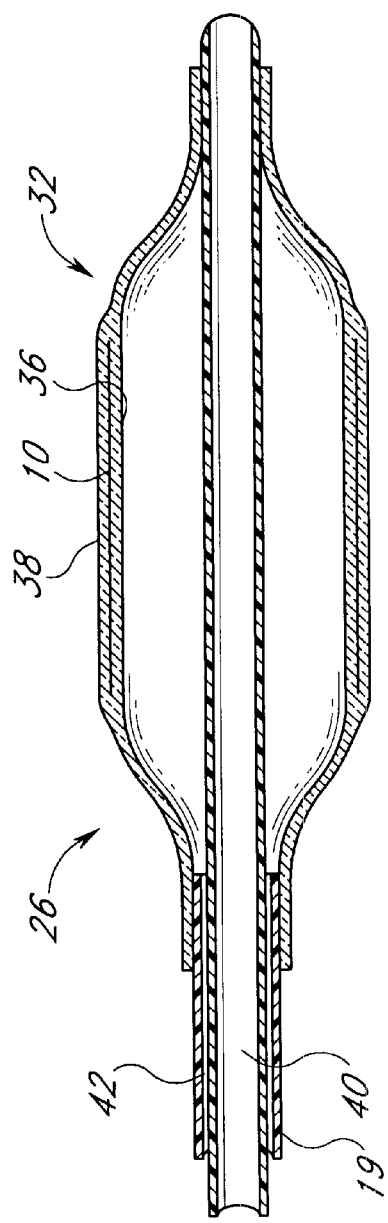
FIG. 4 is an enlarged side elevational cross-sectional view through a balloon incorporating the thin film source of the present invention.

Referring to FIG. 4, there is disclosed a radioactive balloon in accordance with the present invention, configured as in FIG. 3. The balloon 26 comprises a radiation delivery zone 32. The radiation zone 32 comprises an inner balloon wall 36 surrounded by the radiation source 10. Preferably, the radiation source 10 is surrounded by an outer sleeve 38 (sometimes referred to herein as an encapsulant) several embodiments of which are described in additional detail in connection with FIGS. 6 through 9A. In the illustrated embodiment, the radiation source 10 is entrapped between the outer sleeve 38 and balloon wall 36, and the outer sleeve 38 is adhered to the balloon wall 36 or catheter shaft such as through the use of thermal bonding or an adhesive. Suitable adhesives include medical grade UV curable and urethane adhesives known in the art. Any of a wide variety of alternate techniques known to those of skill in the art can also be utilized for securing an outer sleeve 38 to the balloon, sometimes referred to as fusing, heat shrinking, spot welding, and the like.

The sleeve 38 may extend only slightly longer in the axial direction than the axial length of the radiation source 10. The outer sleeve 38 can alternatively extend the entire length of the balloon, or longer, such that it is necked down at the proximal end of the balloon to the catheter shaft and similarly necked down at the distal end of the balloon to the catheter shaft. One outer sleeve 38 comprises 0.0003 inch wall thickness PET tube. Other materials could be polyolefins, nylons, or urethanes, or compounds thereof, and are discussed in detail below.

The balloon 26 is mounted on a tubular body 19, which preferably comprises at least a guidewire lumen 40 and an inflation lumen 42. In the illustrated embodiment, the two lumens 40 and 42 are illustrated in a concentric relationship as is known in the art. Alternatively, the two lumens 40 and 42 can be formed in a side-by-side geometry, (FIG. 5) such as through the use of conventional extrusion techniques.

Figure 5:
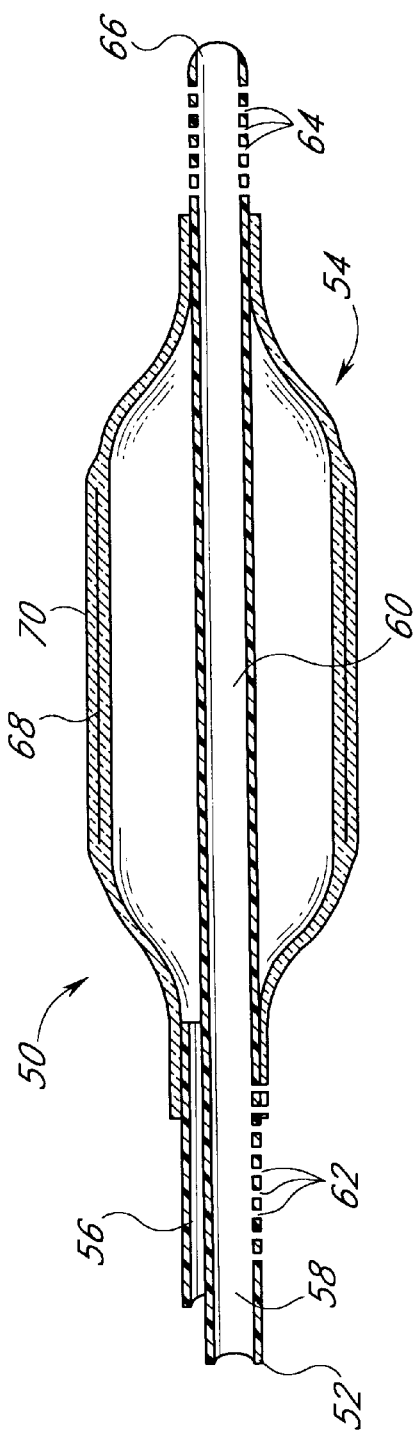
FIG. 5 is an enlarged elevational cross-sectional view of a balloon incorporating the thin film source in accordance with another aspect of the present invention.

Referring to FIG. 5, there is illustrated a perfusion embodiment of the present invention. The radiation delivery catheter with perfusion 50 comprises an elongate flexible tubular body 52 having a distal balloon 54 thereon. In this embodiment the tubular body 52 is preferably configured in a side by side orientation, as is well understood in the catheter art. Thus, the tubular body 52 comprises at least an inflation lumen 56 and a guidewire lumen 58. Additional lumen may be provided, depending upon the desired functionality of the catheter.

The guidewire lumen 58 extends from the proximal guidewire access port (not illustrated) to the distal guidewire access port 66 as is well known in the art. The proximal guidewire access port may either be on the side wall of the catheter as has been discussed in a rapid exchange embodiment, or at the proximal manifold in an over the wire embodiment. A perfusion section 60 of the guidewire lumen 58 extends through the balloon 54, and places a plurality of proximal ports 62 in fluid communication with a plurality of distal ports 64. In this manner, the guidewire (not illustrated) can be proximally retracted within the guidewire lumen 58 to a position proximal to the proximal ports 62 once the balloon 54 has been positioned at the treatment site. The balloon 54 can be inflated by injecting inflation media through the inflation lumen 56, and the perfusion section 60 permits blood to perfuse across the balloon by way of proximal ports 62 and distal ports 64.

As discussed elsewhere herein, the balloon 54 is provided with a thin film source 10 which may comprise one or more layers of radioactive thin film source. The thin film source 10 may be adhered to or otherwise carried by the inside surface or outside surface of the balloon wall and may be further entrapped within an outer tubular layer 70 as illustrated. Alternatively, the thin film source 10 is adhered to or carried by the inside surface or outside surface of the balloon wall without an outer layer 70. Tubular layer 70 preferably is positioned concentrically about the thin film source 10 and heated or otherwise bonded to attach the layer 70 securely to the balloon. The axial length of the tubular layer 70 on, for example, a 3 cm long balloon, may be anywhere within the range of from about 15 mm to about 150 mm measured along the axis of the catheter.

In any of the foregoing embodiments, the isotope layer 16 may comprise either a homogenous isotope population, or a blend of two or more isotopes. For example, a blend may be desirable to achieve a desired combination of half life, activity, penetration or other characteristics in the finished product. Two or three or four or five or more different isotopes may be dispersed uniformly throughout the isotope layer 16, or may be concentrated in different zones along the isotope layer, depending upon the desired activity profile in the finished thin film radiation source.

In accordance with another aspect of the present invention, the thin film radiation source is applied to a delivery structure such as a balloon in a manner that permits radially asymmetric delivery. This may be desirable for treating only a selected site within the circumference of the arterial wall, such as in the case of an eccentric stenosis.

In this embodiment radioisotope is provided only along a portion of the circumference of the delivery structure such as a balloon. The radioisotope zone may comprise anywhere in the range of from about 10% to about 70% of the total circumference of the balloon, and, in one embodiment, is within the range of from about 30% to about 50% of the total circumference of the balloon. This may be accomplished in any a variety of manners, such as masking the thin film prior to application of the isotope, applying a blocking layer to block release of radiation from portions of the circumference, and the like as will be apparent to those of skill in the art in view of the disclosure herein. In one embodiment, a thin film sheet is prepared as has been described herein, except that radioisotope is only adhered to the thin film substrate in a series of discrete zones which are separated by nonradioactive portions of substrate. The radioactive zones can be spaced apart along the substrate sheet to correspond to the circumference of the delivery balloon, so that when the radioactive thin film is wrapped around the balloon, the radioactive zones align with each other to provide a radioactive stack on only a predetermined circumferential portion of the balloon.

Thus, at least a first and a second zone can be provided on the thin film source in accordance with the present invention. In one embodiment the first zone is radioactive and the second zone is not radioactive. In another embodiment, the first zone has a first radioactive activity and the second zone has a second, lesser radioactive activity. Alternatively, other characteristics of the radioactive source can be varied between the first zone and the second zone, depending upon the desired delivery performance.

In accordance with another aspect of the present invention, the balloon catheter may be constructed which allows for delivery of radiation to differing sizes of lumens. In such a device, the balloon preferably comprises a compliant plastic material. The substrate for the source may be either the balloon itself or another thin film of a compliant or elastomeric plastic. As the pressure inside the compliant balloon is increased, the outer diameter of the balloon will increase. Thus, a single balloon catheter may be used to treat different size lumens by simply varying the pressure and hence the inflation diameter of the balloon.

The increase in diameter will result in a decrease in density of isotope atoms per surface area. By adjusting the dwell time, the predetermined dosage can be delivered. For example, a 20 mm balloon having an outer diameter of 2.0 mm and $10^{17}$ atoms of isotope on the surface will result in a density of $7.96 \times 10^{14}$ atoms/mm$^2$. If this balloon were pressurized to increase to a 2.5 mm diameter, the density would decrease to $6.34 \times 10^{14}$ atoms/mm$^2$. This is a 20% decrease, resulting in a need for a 20% increase in dwell time to achieve an equivalent dose. There may also be a slight decrease in balloon length with increased diameter of infla-tion. This change, however, is dependent on the level of compliance and may be negligible in most cases, but is easily remedied by careful selection of balloon size.

Figure 6:
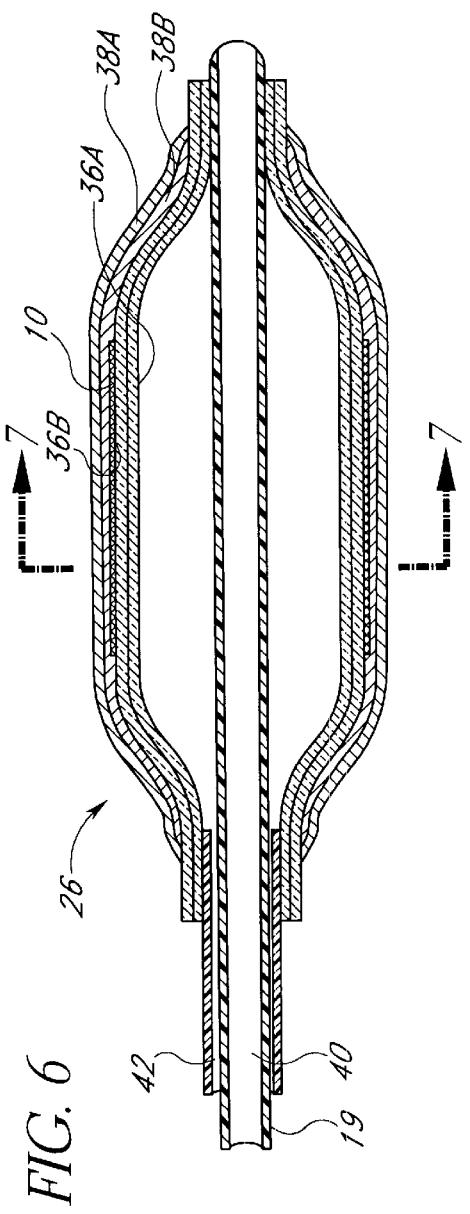
FIG. 6 is an enlarged side elevational cross-sectional detail view through a balloon incorporating the multi-layered sealed source embodiment of the present invention.
Figure 7:
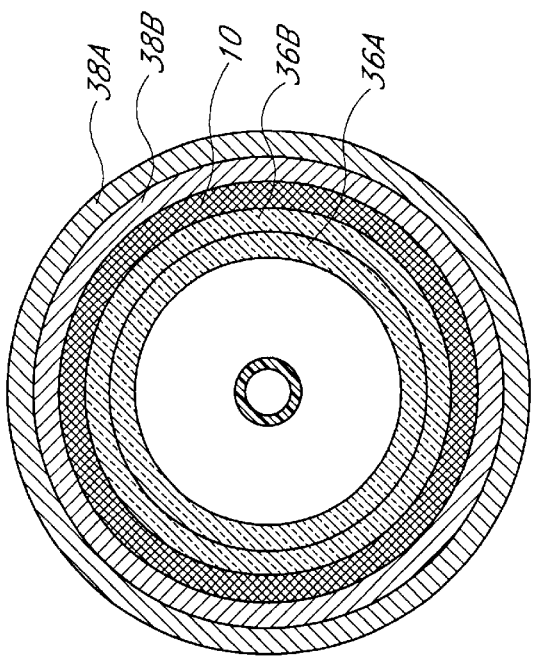
FIG. 7 is a cross-section taken along the line 7—7 in FIG. 6.

Details of an outer layer configuration for enhancing the seal for containing the radioactive source are illustrated in FIGS. 6 and 7. The present inventors have determined that one reason for failure of certain radiation delivery balloon designs to adequately contain the isotope is due to the separation of the cover sheet from the balloon or catheter shaft at the axial ends of the balloon. The repeated inflation and deflation which is common to dilatation procedures and/or regulatory approval protocols can cause a separation at the bond between the cover sheet and the balloon. The failure of the cover and the balloon to hold together is typically due to materials disclosed in the prior art for use as balloon and cover sheet elements, such as polyethylene, nylon and polyethylene terephthalate. These materials, as previously disclosed, provide a mechanical seal rather than a chemical or fused seal to the catheter shaft and underlying balloon. Thus, heat and adhesives are utilized to create mechanical bonds which lack sufficient stability when they are worked in the manner often required during balloon inflation and deflation.

In accordance with the present invention, the encapsulant cover layer and the balloon materials are fused together at least on either side of the source. A "fused" attachment as that term is used herein is readily distinguishable from purely mechanical attachment (e.g. heat shrink or adhesive bonding), wherein the layers may become delaminated or otherwise separated as a consequence of excessive pressure or inflation cycling. In a "fuse" type of attachment, the two or more starting layers cannot be peeled apart without tearing through and the line between the original layers is oftentimes partially or completely obscured. A fuse as contemplated in the context of the present invention thus has a significantly reduced risk of separation or delamination during use, and may therefore be worked by inflation and deflation without separation. An outer sleeve such as sleeve 38 or other encapsulant disclosed herein is at least fused to an underlying surface on each of the proximal and distal ends of the source to encapsulate the source in a cylindrical envelope carried by the balloon. In a preferred embodiment, the fused seal extends throughout the entire axial length of the source such that fluid will not be drawn between layers enveloping the source should any such layers be punctured and then inflated and deflated. The fused bond may be formed between at least some of the layers, such as between the outer cover and the balloon, to provide a sealed encapsulated source on the balloon.

In accordance with one aspect of the invention, a polyethylene tube is first extruded and then coextruded with an ethyl methacrylate (EMA) layer over the PE to form a PE balloon with an EMA bonding layer, or the two materials are coextruded together. The extrusion process, performed at about 300–400° F., leads to a complete attachment between the EMA and PE that can undergo the balloon forming process without forming gaps or voids in the EMA layer. The cover tube is formed in the same way as the balloon, only the EMA is the first (inner) layer and the PE is the second (outer) coextruded layer.

The balloon is thereafter attached to the catheter shaft according to methods well known to catheter manufacturers and discussed elsewhere herein. After the source and cover layer are assembled onto the balloon, the entire assembly can be heat fused. At this point, the EMA layer of the PE balloon directly opposes the EMA layer on the PE encapsulant layer proximally and distally of the source, forming a PE-EMA-EMA-PE stack. In embodiments where the source also comprises EMA or a material with similar melting point characteristics, the EMA layers of the balloon and encapsulant fuse together along the length of the source as well, forming an EMA fuse layer 72 with the isotope suspended therein, as illustrated in FIG. 8. Since the EMA melts at a much lower temperature than the crosslinked PE, the cover can be heat fused in a mold under moderate temperatures (200–300° F.) and pressures (1–4 ATM) without damaging the balloon. An annular fused seal is thus formed at least both proximally and distally of the source to fully encapsulate the source within the wall of the multilayer balloon. In the case of a source having compatible fusing surfaces, the seal continues throughout the source length increasing the strength of the body of the balloon from about 120 psi to about 210 psi.

EXAMPLE 1

One set of ten samples constructed with a PE-EMA-source-EMA-PE stack as described above but with an annular source layer which is not fusable with the EMA was placed in an experimental fixture capable of repeatedly inflating and deflating the balloon. The PE was 0.00052" thick and the EMA was 0.000052" thick. Each balloon/source was 2.5 mm in diameter and 22 mm in length. The balloon was submerged within a test tube containing a methylene blue dye (0.5%) in order to detect separation between the cover and balloon layers. The balloons were inflated to 3 ATM and deflated after 5 seconds for over 250 cycles without detecting any leaks. A second set of ten samples constructed with gaps at the balloon necks using misformed encapsulant and little or no heat fusion in the EMA layer were similarly tested and each sample leaked after 10–20 cycles.

EXAMPLE 2

A set of ten samples constructed as described above (PE-EMA-source-EMA-PE stack) with source activities in the 1 mCi range were constructed and tested as above. The PE-EMA-EMA-PE stack extended proximally of the source for about 5 mm and distally of the source for about 5 mm. The devices were first wipe tested to establish that no removable surface activity was present on the samples. The test tubes containing one balloon each were removed from the fixture every twenty cycles and surveyed with a Geiger counter for removed activity. No removed activity was found after 200 cycles.

Thus, one embodiment of the sealed source configuration in accordance with the present invention is schematically illustrated at FIGS. 6 and 7. In these figures, the bonding surfaces are shown for clarity as discrete layers 36b and 38b. In preferred embodiments, however, the layers 36b and 38b would be fused together on at least a portion of their lengths and preferably throughout the length of the source such that the interface between the layers would be partially or fully obscured.

In the illustrated embodiment, a radioactive source 10 is encapsulated between a balloon 36 and an outer encapsulant 38 as has been described. In the illustrated embodiment, however, the balloon comprises an inner support layer 36a and an outer bonding surface 36b. The encapsulant 38 comprises an inner bonding surface 38b and an outer support layer 38a. As illustrated, bonding surface 36b from the balloon is in contact with bonding surface 38b both proximally and distally of the radiation source 10. The source includes an isotope, and may comprise a single layer or a multilayer stack as is discussed elsewhere herein. This structure at least enables a fused annular seal beyond the axial ends of the source. A further embodiment provides a seal completely through the source zone. This can be accomplished by forming the source out of appropriate materials.

In one polyethylene embodiment, the outer encapsulant support layer 38a comprises polyethylene and the bonding layer 38b comprises EMA. The inner balloon support layer 36a comprises polyethylene and the balloon bonding layer 36b comprises EMA. This construction permits a fused seal between the encapsulant and the balloon, as has been discussed, to prevent leakage of radioisotope.

A schematic diagram showing assembly of a sealed source is illustrated in FIG. 8. An extruded tube 44 comprised of an outer bonding layer 36b, preferably of EMA over an inner structural layer 36a preferably of PE, which forms the balloon, has the radiation source layer 10 placed or formed thereon. The coextruded cover tube 46, comprised of an inner bonding layer 38b, preferably of EMA, and an outer structural layer 38a, preferably of polyethylene, is placed over the tube 44. Following application of heat and at least a slight pressure to ensure contact between the bonding layers, the sealed source 48 is formed, in which the two bonding EMA layers 36b and 38b have fused to form a single layer 72 with the isotope suspended therein.

In its simplest form, the source comprises an isotope attached to or carried on a bonding layer. Due to the physical properties of most suitable bonding materials (low softening or melt point), the source preferably also includes at least one layer having greater structural integrity than the bonding layer. This construction can be accomplished in three portions or layers: two bonding layers (B) with an isotope-containing layer (I) between them, or (B)-(I)-(B) in shorthand. It may be desirable to add an additional support layer (S) to one or both bonding layers to provide greater support to the source for ease of processing or use, if the assembly is not otherwise sufficiently supportive for a given application. Such sources would be, in shorthand, (SB)-(I)-(B), (B)-(I)-(BS), or (SB)-(I)-(BS). The bonding layers all comprise fusable and preferably a common material.

The materials which form the structural layers and bonding layers preferably have one or more characteristics which aid the layers performing their functions within the structure. The bonding layer and support layer materials preferably have a strong bond between them. A strong bond may be the result of chemical or mechanical attachment, or some combination of the two, and it may be achieved by coextrusion or coinjection of the materials. It may also be achieved by casting one material over the other or injection molding one material over the other. Attachment of the materials may also be enhanced if the bonding and support layers have at least one material in common (e.g. a small amount of the support layer material is incorporated into the material which forms the bonding layer). Another preferred characteristic is for the melting or softening points of the bonding layer and support layer to differ, with the melting or softening point of the bonding layer being the lower of the two. This allows for the structure or shape of the source to be maintained by the support layer(s) when the bonding layers are fused by the application of heat. In some embodiments, it is preferred that the support layer material be generally non-compliant.

In preferred embodiments, the isotope-containing layer (I) above is a multilayer isotope-containing substructure or radiation source which can be combined with one or more bonding layers or bonding-support stacks (SB) and assembled into a larger structure. For example, when the radiation delivery source is the balloon of a balloon catheter, it may be desirable to prepare the isotope-containing substructure portion of the source separately. Following its preparation, the isotope-containing substructure, preferably in a tubular form or a rolled-up sheet, is then placed upon the balloon of a balloon catheter and then covered with a single or multilayer encapsulant structure and heated to fuse the bonding layers. Pressure may also be placed on the assembled stack such as by inflation within a capture tube with heating to further facilitate the fusing process. In another embodiment, the source may comprise two substructures, a balloon and an encapsulant, wherein the encapsulant substructure incorporates the isotope-containing layer.

By using source preparation methods as described above, the non-radioactive substructures may be prepared ahead of the time of use and then assembled with a recently-made isotope containing portion of the source just prior to use or shipment. Thus, one may create separate subassemblies or substructures and assemble them just prior to shipment or use of the catheter device. Although the discussion which follows is in terms of a balloon catheter and a tubular source, one skilled in the art would recognize that the source may be used for applications other than a balloon and that the same concepts apply to other geometries such as a sheet.

Thus, in one embodiment, the isotope-containing multilayer substructure may simply comprise a bonding layer-isotope (BI) two layer stack. If this substructure were assembled into a source with a balloon and encapsulant, each of which comprise a bonding layer and a structural layer, the source would have the following layer structure: (SB)-(BI)-(BS). Alternatively, one can protect the isotope-containing layer of the substructure from damage during later processing by applying a coating layer (C) to the isotope-containing layer and/or other exterior layer, such as is described supra, to form sources of the type (SB)-(BIC)-(BS), and (SB)-(CBIC)-(BS). In preferred embodiments, the coating layer is the same material as or is heat fusable to the bonding layers.

In other embodiments, the isotope-containing substructure further comprises a structural layer, such as to aid in formation and processing of the source. Thus the substructure could take the form (BSI) or (SBI), with the latter being preferred such that when it is combined with the other portions to form the full multilayer source, the bonding layer upon which the isotope-containing layer sits can fuse with the bonding layer on either the balloon or the encapsulant. In the latter structure, (SBI) it is preferred that there be an additional bonding layer (BSBI) such that the substructure bonding layers may fuse with bonding layers on both the balloon and encapsulant. Substructures containing support layers may also have an additional protective coating layer on the isotope-containing layer, eg. (BSIC), (CBSIC), (SBIC), (BSBIC), and (CBSBIC).

In accordance with the present invention, one preferred embodiment of the source is represented by the shorthand (SB)-(CBSBIC)-(BS). A source of this type is shown in FIG. 9. FIG. 9 is an exploded cross-section showing the source during the assembly of the three portions: encapsulant, isotope-containing substructure, and balloon. The upper two layer portion is the encapsulant comprising a bonding layer 38b and a structural layer 38a. The lower two layer portion is the balloon comprising a bonding layer 36b and a structural layer 36a. The isotope-containing substructure or radiation source 10 initially comprises seven layers. The core of the substructure is a three layer stack comprising a structural layer 74a sandwiched between two bonding layers 74b. On one bonding layer sits the isotope containing layer, which is a two layer structure comprising a tie layer 14 and an isotope layer 16. The isotope layer 16 preferably comprises a metal salt or oxide with at least one isotope. The tie layer 14 and isotope layer 16 is of the type described supra and as such, there may not be a clear visual distinction between the layers. The outer layers of the substructure are coating layers 17.

FIG. 9A illustrates the final configuration of the source of the type in FIG. 9, following the application of heat, either with or without pressure, to fuse the various bonding layers. The source of FIG. 9A comprises two layers of fuse 72 sandwiched among the structural layers of the balloon 36a, isotope-containing substructure 74a, and encapsulant 38a. The upper layer of fuse 72, between the isotope-containing substructure 74a and encapsulant 38a support layers, is that which has the isotope embedded therein.

To aid in the formation of the complete fuse through coating layers and isotope-containing layers, the materials which form those layers preferably have a melting point similar to that of the bonding materials, comprise a material common with the bonding materials, or have some other physical or chemical property which aids them to become part of a fuse layer 72. Alternatively, the coating layers and/or isotope-containing layers may be porous or comprise a plurality of apertures through which the bonding materials may form fuses or spot welds to bind the layers together.

Thus, using the principles described above, a wide variety of multilayer sources encompassed within the present invention can be prepared by combining layers, creating substructures, and fusing bonding layers in the multilayer stacks formed.

In the above multilayer sources, the fuse between the bonding layer adjacent to the isotope-containing layer in the substructure and the bonding layer in either the balloon or encapsulant may extend through the isotope-containing layer such that the isotope-containing layer is suspended within a larger layer of bonding material, as shown in FIG. 8. FIG. 8 depicts a tubular structure, as would exist in a tubular source or in a cross-section of the center portion of one embodiment of balloon catheter incorporating a sealed source of the present invention. Such a fully radially extending fuse may be enhanced for certain materials if the isotope-containing layer is permeable or has gaps therein, such that it does not create a barrier to the fusing of the two bonding layers. This is a benefit in that even in the case of a tear such as by calcium or a stent strut, only the edge surface area of the tear would be exposed to the bloodstream.

In experiments, balloons having a full seal were punctured and then inflated and deflated several times in a blue dye solution to determine the degree of infiltration of fluid into the breach. After several cycles of inflation and deflation, the dye solution could be seen filling the channel formed by the needle which created the puncture. There was, however, no separation of fused layers adjacent to the puncture and no lateral infiltration of dye solution between fused layers of the source, indicating that the solution was exposed to only that small portion of the edge of the source in the puncture channel itself. In addition, the completely fused structure increases the surface area of fuse and decreases the potential of a seal breach due to overhandling.

The optimal balloon bonding surface 36b and encapsulant bonding surface 38b can be determined through routine experimentation by those of ordinary skill in the art in view of the disclosure herein, and depending upon the desired balloon 36a material and encapsulant 38a material. In addition, variations can be made on the foregoing stack depending upon the construction materials and the desired process parameters, particularly temperature, for a given balloon construction. In general, the desired result is a fused or blended polymeric material along the length of the radiation source 10, such as may be readily accomplished through heating certain types of materials under compression. This may be accomplished in a 4-layer stack (not counting the source) as illustrated where the balloon material 36a and encapsulant material 38a will not fuse as has been described herein. Alternatively, a 2-layer stack may be used where the balloon material 36a and the encapsulant material 38a will fuse to form a sealed bond. A 3-layer stack such as a balloon 36a, an encapsulant 38a, and one of 36b or 38b may be positioned therebetween, either radially inwardly from or radially outwardly from the radiation source 10.

The encapsulant 38 may extend any of a variety of lengths along the balloon 26, to produce proximal and distal annular seals of the desired length. In the illustrated embodiment, the encapsulant 38 extends beyond the working length of the balloon by about 5–8 mm in each of the proximal and distal directions to maximize the total surface area of the proximal and distal seals. The encapsulant 38 may extend proximally farther than the balloon neck, and distally farther than the balloon neck if desired. Encapsulant lengths of only slightly longer than the axial length of the source 10 may also be utilized, provided the materials of the stack provide a sufficient seal over the shortened axial length.

The fused encapsulant layer in accordance with the present invention can be utilized to provide a sealed source using a source produced by any of a variety of isotope attachment techniques. Thus, in addition to using the various binding chemistries disclosed supra, the source layer 10 may comprise any of a variety of alternative chemistry schemes, including chelating chemistry reactions, ion implantation, and others as will be understood by those of skill in the art.

In accordance with the method of the present invention, a balloon catheter such as any described above is percutaneously inserted and transluminally advanced through a patient's vasculature, to the treatment site. At the treatment site, the balloon is expanded to position the radioactive delivery layer against the vessel wall. The balloon remains expanded for a sufficient radiation delivery time, and is thereafter deflated and withdrawn from the patient. The balloon may be introduced through an introduction sheath, which can be proximally withdrawn to expose the balloon once the balloon has been positioned at the treatment site.

If delivery times greatly in excess of 3–4 minutes are clinically desirable, the catheter 18 may be provided with a perfusion conduit such as that illustrated in FIG. 5. Any of a variety of perfusion structures can be utilized, such as any of those disclosed in U.S. Pat. No. 5,344,402 to Crocker entitled Low Profile Perfusion Catheter or U.S. Pat. No. 5,421,826 to Crocker et al. entitled Drug Delivery and Dilatation Catheter Having a Reinforced Perfusion Lumen, the disclosure of each of which is incorporated in its entirety herein by reference.

In accordance with another aspect of the method of the present invention, the radiation delivery and balloon dilatation catheter of the present invention is utilized to simultaneously dilate a stenosis in a vessel and deliver a treating dose of radiation. The catheter is percutaneously introduced and transluminally advanced through the arterial system to reach a stenosis. The balloon is positioned within the stenosis, and inflated to expand the stenosis as is known in the art. During the expansion step, the balloon is delivering a treatment dose of radiation to the vessel wall. The balloon may then be left in position in the inflated profile optionally with perfusion for a sufficient period of time to deliver the desired dose of radiation. The balloon is thereafter deflated, and the catheter is withdrawn from the treatment site.

In accordance with a further aspect of the method of the present invention, the radiation delivery catheter of the present invention may be utilized to simultaneously implant a stent while delivering a dose of radiation. In accordance with this aspect of the method, a stent is positioned on the radiation delivery balloon prior to percutaneous insertion within the patient. The balloon carrying a stent thereon is thereafter percutaneously inserted and transluminally advanced through the patient's vasculature to the treatment site. The balloon is expanded at the treatment site to expand the stent, while simultaneously delivering a dose of radiation. The balloon is thereafter deflated, and withdrawn from the patient, leaving the expanded stent in position at the site.

In accordance with another aspect of the present invention, there is provided a method of treating a previously implanted stent or graft with exposure to a dose of radiation. The method comprises the steps of identifying a previously implanted stent or graft within a body lumen. A radiation delivery catheter of the type described elsewhere herein is positioned within the stent or graft, and the balloon is inflated to position the radioactive source against or near the interior wall of the stent or graft. The balloon may either be inflated to a sufficient pressure to further dilate the stent or graft, or inflated sufficiently to position the radiation source against the interior wall of the stent or graft without additional stent or graft expansion or sizing. Following delivery of a dose of radiation, the balloon is deflated and removed from the patient.

Any of the foregoing methods may be accomplished either with or without the perfusion capability disclosed elsewhere herein. In addition, any of the foregoing methods may be accomplished through the use of an over the wire embodiment of the invention or a rapid exchange embodiment of the invention as has been disclosed elsewhere herein.

Thus, in accordance with the present invention, there is provided a catheter having a radiation delivery layer on the balloon, which permits a relatively low energy thin film source to be positioned directly against, or within about 0.001 inches and preferably no more than about 0.003 inches from the vascular wall, depending upon the thickness of any outer sleeve 38 or 70 or other coating. In addition, the present configuration expels substantially all blood or other fluids from between the radiation source and the vessel wall, throughout the entire interior circumference of the vessel for the axial length of the balloon. As a consequence, the radiation is not required to penetrate multiple structures as well as blood within the vessel in order to reach the vessel wall. In addition, radiation delivery is essentially uniform throughout the entire circumference of the vessel at the delivery site.

The configuration of the balloon of the present invention is such that the radiation delivery layer does not need to be elastic and can simply be folded with the balloon material into the reduced, insertion profile. Higher radiation dosages than those specifically described herein can be readily achieved, such as through the use of longer dose times and/or higher activity isotopes and/or higher density of the isotope layer and/or more layers of the thin film source.

Although the present invention has been described in terms of certain preferred embodiments, other embodiments of the invention will become apparent to those of skill in the art in view of the disclosure herein. Accordingly, the scope of the present invention is not intended to be limited by the foregoing, but rather by reference to the attached claims.

What is claimed is:

1. A multilayer radiation delivery source comprising:
   a first bonding layer having a first side;
   a second bonding layer, having a second side which faces toward the first side; and
   an isotope layer in between the first side and the second side, wherein the isotope layer comprises a metal salt or metal oxide and at least one radioactive isotope species;
   wherein the first side and the second side are secured together through the isotope layer to produce a multilayer radiation delivery source.

2. The source of claim 1, wherein said isotope is a gamma emitting isotope and/or a beta emitting isotope.

3. The source of claim 1, wherein the isotope comprises at least one isotope selected from the group consisting of P-32, I-125, Pd-103, W/Re-188, As-73, and Gd-153.

4. The source of claim 1, further comprising a structural layer on at least one of the first and second bonding layers.

5. The source of claim 1, wherein the source comprises a sheet having a total thickness of no more than about 0.003 inches.

6. The source of claim 1, wherein the source comprises a tube having a total wall thickness of no more than about 0.003 inches.

7. The source of claim 1, further comprising a first structural layer on the first bonding layer and a second structural layer on the second bonding layer.

8. The source of claim 7, wherein the first and second bonding layers are fused together to provide a continuous seal from proximally of to distally of the isotope layer.

9. The source of claim 7, further comprising a coating layer on the isotope layer.

10. The source of claim 9, wherein the coating layer comprises at least one material selected from the group consisting of cyanoacrylates, acrylics, acrylates, acrylic acid, urethanes, polybutyl vinyl chloride, polyvinylidene chloride, and polyethylene.

11. The source of claim 7, wherein at least one of the first and second structural layers comprises a material selected from the group consisting of polyamide, polyethylene, polyester, polyethylene terephthalate, and polyvinyl chloride.

12. The source of claim 11, wherein the first and second bonding layers comprise ethylene methyl acrylate.

13. The source of claim 12, wherein the first and second structural layers comprise polyethylene.

14. The source of claim 12, wherein the first and second bonding layers are sufficiently adhered together that they can not be manually delaminated from each other without tearing.

15. The source of claim 12, comprising at least one co-extrusion of EMA and PE, or EMA and polyurethane.

16. A radiation delivery balloon catheter, comprising:
   an elongate flexible tubular body, having a proximal end and a distal end;
   an inflatable balloon on the tubular body near the distal end thereof, said balloon in fluid communication with an inflation lumen extending axially through the tubular body;
   a balloon bonding surface carried by the outer surface of the balloon;
   a radiation source on the balloon bonding surface, wherein the radiation source comprises a metal salt or metal oxide and at least one radioactive isotope species; and
   an encapsulant surrounding the radiation source, the encapsulant having at least an encapsulant bonding surface on its radially inwardly facing surface for fusing with the balloon bonding surface at least proximally and distally of the radiation source.

17. A radiation delivery balloon catheter as in claim 16, wherein the balloon bonding surface comprises ethylene methyl acrylate.

18. A radiation delivery balloon catheter as in claim 17, wherein the encapsulant bonding surface comprises ethylene methyl acrylate.

19. A radiation delivery balloon catheter as in claim 16, wherein the encapsulant comprises an outer polyethylene layer and an inner ethylene methyl acrylate layer.

20. A radiation delivery balloon catheter as in claim 16, wherein all bonding surfaces comprise the same material.

21. A radiation delivery balloon catheter as in claim 16 wherein the source further comprises a tie layer for binding with an isotope.

22. A radiation delivery balloon catheter as in claim 16, wherein the source comprises at least one source bonding layer to permit a continuous bond between the source and at least one of the encapsulent and the balloon bonding surface from proximally of the source to distally of the source.

23. A radiation delivery balloon catheter as in claim 16, further comprising a guide wire lumen extending axially throughout at least a distal portion of the tubular body.

24. A radiation delivery balloon catheter as in claim 23 further comprising a proximal guide wire access port on the tubular body, positioned within about 35 cm of the distal end of the tubular body.

25. A radiation delivery balloon catheter as in claim 16, further comprising a perfusion conduit extending through the tubular body from a proximal side of the inflatable balloon to a distal side of the inflatable balloon, at least a first perfusion port on the tubular body on the proximal side of the balloon and at least a second perfusion port on the distal side of the balloon.

26. A radiation delivery balloon catheter as in claim 25, wherein the perfusion conduit comprises a distal portion of a guidewire lumen.

27. A method of treating a site within a vessel, comprising the steps of:
   identifying a site in a vessel to be treated;
   providing a radiation delivery catheter having an expandable balloon with a thin film radiation source thereon, said thin film comprising a substrate layer having an isotope layer thereon, said isotope layer comprising a metal salt or a metal oxide and at least one radioactive isotope species, wherein said isotope layer is encapsulated by an outer encapsulant layer fused to the substrate throughout the length of the source;
   positioning the balloon within the treatment site;
   inflating the balloon within the treatment site;
   delivering a dose of radiation from the delivery balloon to the treatment site; and
   thereafter deflating the balloon and removing the balloon from the treatment site.

28. The method of claim 27, wherein said catheter has an isotope loss of no more than 5nCi throughout the period between the positioning step and the removing step.

29. A method of treating a site within a vessel as in claim 27, wherein said site comprises a previously implanted prosthesis, and the positioning the balloon step comprises positioning the balloon at least partially within the prosthesis.

30. A method of treating a site within a vessel as in claim 29, wherein the prosthesis comprises a stent.

31. A method of treating a site within a vessel as in claim 29, wherein the prosthesis comprises a graft.

32. A method of treating a site within a vessel as in claim 27, wherein the radiation delivery catheter further comprises an expandable stent on the balloon, and wherein the inflating the balloon step comprises inflating the balloon within the treatment site to implant the stent at the treatment site and simultaneously delivering radiation from the thin film into the vessel wall.

33. A method of treating a site within a vessel as in claim 27, further comprising the step of perfusing blood from a first side of the balloon to a second side of the balloon during the delivering a dose of radiation step.

34. A method as in claim 27, wherein the vessel is a large artery or vein.

35. A method of simultaneously performing balloon dilatation of a stenosis in a body lumen and delivering radiation to the body lumen, comprising the steps of:
identifying a stenosis in a body lumen;
providing a treatment catheter having an elongate flexible tubular body with an inflatable balloon near the distal end thereof, a cylindrical thin film radiation delivery layer on the balloon, said radiation delivery layer comprising a metal salt or a metal oxide and at least one radioactive isotope species, an encapsulant layer over the radiation delivery layer, a continuous seal between the encapsulant, the delivery layer and the balloon along at least the length of the radiation delivery layer;
transluminally advancing the balloon through the lumen;
positioning the balloon within the stenosis;
inflating the balloon to radially expand the lumen in the area of the stenosis; and
simultaneously delivering radiation from the thin film into the lumen wall.

36. A method of simultaneously performing balloon dilatation of a stenosis in a body lumen, delivering a stent, and delivering radiation to the body lumen, comprising the steps of:
identifying a stenosis in a vessel;
providing a treatment catheter having an elongate flexible tubular body with an inflatable balloon carrying an expandable stent near the distal end thereof, and a cylindrical thin film radiation delivery layer on the balloon, said radiation delivery layer comprising a metal salt or a metal oxide and at least one radioactive isotope species, an encapsulant layer over the radiation delivery layer, a continuous seal between the encapsulant, the delivery layer and the balloon along at least the length of the radiation delivery layer;
transluminally advancing the balloon through the vessel;
positioning the balloon within the stenosis;
inflating the balloon to radially expand the vessel in the area of the stenosis; and simultaneously expand and deliver the stent; and
delivering radiation from the thin film to the vessel wall.

37. A multilayer radiation delivery source, comprising:

a first portion comprising a first support layer having a first bonding layer thereon;
a second portion comprising a second support layer having a second bonding layer thereon; and
a third portion comprising an isotope layer comprising a metal salt or a metal oxide and at least one radioactive isotope species;
wherein the third portion lies between the first and second bonding layers and the first and second bonding layers begin to melt at a different temperature than the first and second support layers.

38. The multilayer radiation delivery source of claim 37, wherein the first and second bonding layers begin to melt at a lower temperature than the first and second support layers.

39. A method of irradiating a site within a lumen, comprising the steps of:
providing a radiation delivery catheter having an expandable support with a thin film radiation source thereon, said thin film comprising a substrate layer having an isotope layer thereon, said isotope layer comprising a metal salt or a metal oxide and at least one radioactive isotope species, wherein said isotope layer is encapsulated by an outer encapsulant layer fused to the substrate throughout the length of the source;
positioning the support within a site within a lumen;
radially expanding the support within the site;
delivering a dose of radiation from the thin film radiation source to the site;
radially contracting the support; and
removing the support from the site.

40. A method as in claim 39, wherein said site comprises a previously implanted prosthesis, and positioning the support comprises positioning the radiation source at least partially within the prosthesis.

41. A method as in claim 40, wherein the prosthesis comprises a stent or graft.

42. A method as in claim 39, wherein radially expanding the support comprises inflating an inflatable balloon.

43. A method as in claim 39, further comprising perfusing a fluid from a proximal side of the expandable support to a distal side of the expandable support while the support is expanded.

44. A method as in claim 39, wherein the radiation delivery catheter further comprises an expandable stent on the support, and wherein radially expanding the support further comprises implanting the stent at the site and simultaneously delivering radiation from the thin film into the lumen wall.

45. A method as in claim 39, wherein said isotope comprises a gamma emitting isotope and/or a beta emitting isotope.

46. A method as in claim 39, wherein the radioactive isotope comprises an isotope selected from the group consisting of P-32, I-125, Pd-103, W/Re-188, As-73, and Gd-153.

47. A method as in claim 39, wherein the lumen is selected from the group consisting of large and small arteries, large and small veins, hollow organs, surgically created pathways, esophagus, trachea, urethra, ureters, fallopian tubes, intestines and colon.

* * * * *